(12) United States Patent
Ishikawa

(10) Patent No.: US 11,020,281 B2
(45) Date of Patent: Jun. 1, 2021

(54) METHOD FOR FORMING STRETCHABLE STRUCTURE FOR ABSORBENT ARTICLE AND STRETCHABLE STRUCTURE FOR ABSORBENT ARTICLE

(71) Applicant: DAIO PAPER CORPORATION, Ehime (JP)

(72) Inventor: Yasuko Ishikawa, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 1059 days.

(21) Appl. No.: 15/511,364

(22) PCT Filed: Aug. 19, 2015

(86) PCT No.: PCT/JP2015/073222
§ 371 (c)(1),
(2) Date: Mar. 15, 2017

(87) PCT Pub. No.: WO2016/047320
PCT Pub. Date: Mar. 31, 2016

(65) Prior Publication Data
US 2017/0281417 A1    Oct. 5, 2017

(30) Foreign Application Priority Data
Sep. 26, 2014    (JP) .............................. JP2014-197469

(51) Int. Cl.
*A61F 13/15* (2006.01)
*A61F 13/496* (2006.01)
(Continued)

(52) U.S. Cl.
CPC ........ *A61F 13/15739* (2013.01); *A61F 13/15* (2013.01); *A61F 13/15593* (2013.01);
(Continued)

(58) Field of Classification Search
CPC .......... A61F 13/15739; A61F 13/15593; A61F 13/15699; A61F 13/49011;
(Continued)

(56) References Cited

U.S. PATENT DOCUMENTS 6,291,039 B1 * 9/2001 Combe ................ A41D 27/245
428/35.2
9,333,119 B2 * 5/2016 Zink ................ A61F 13/15699
(Continued)

FOREIGN PATENT DOCUMENTS

EP    1666178 A1    6/2006
JP    5-15551 A    1/1993
(Continued)

OTHER PUBLICATIONS

Machine translation of JP 2008-104853 (date unknown).*

*Primary Examiner* — John L Goff, II
(74) *Attorney, Agent, or Firm* — Muncy, Geissler, Olds & Lowe, P C.

(57) ABSTRACT

The present invention is intended to prevent cutting of the resilient and elastic members by a welding process. The foregoing issue is solved by passing a first sheet layer, a second sheet layer, and elongated resilient and elastic members continuously disposed in an MD direction between the two sheet layers, between a first roll with joint convex parts provided at circumferential intervals on an outer peripheral surface and a second roll opposed to the first roll, and pressurizing and heating the first sheet layer and the second sheet layer to form sheet joined sections by welding the first sheet layer and the second sheet layer in such a manner as to cross the resilient and elastic members and have MD-direction intervals therebetween, wherein circumferentially continuous grooves are formed on a pressurization surface of the second roll, passage sections of the resilient and elastic members are pressurized and heated in positions
(Continued)

including the grooves of the second roll, and non-passage sections of the resilient and elastic members are pressurized and heated in positions not including the grooves of the second roll.

4 Claims, 16 Drawing Sheets

(51) Int. Cl.
*A61F 13/49* (2006.01)
*B29C 65/02* (2006.01)
*B29C 65/48* (2006.01)
*B29L 31/48* (2006.01)

(52) U.S. Cl.
CPC ............ *A61F 13/49* (2013.01); *A61F 13/496* (2013.01); *A61F 13/49012* (2013.01); *A61F 13/49019* (2013.01); *A61F 13/4963* (2013.01); *B29C 65/02* (2013.01); *B29C 65/4815* (2013.01); *A61F 2013/15715* (2013.01); *A61F 2013/49053* (2013.01); *A61F 2013/49088* (2013.01); *B29L 2031/4878* (2013.01)

(58) Field of Classification Search
CPC .......... A61F 13/49012; A61F 13/49014; A61F 13/49015; A61F 13/49017; A61F 13/49019; A61F 13/49061; A61F 13/51464; A61F 13/4902; A61F 13/496; A61F 13/49009; A61F 13/4963; A61F 2013/15715; A61F 2013/49053; A61F 2013/49088; A61F 2013/4878; A61F 2013/15878; B29C 65/08; B29C 65/083; B29C 65/084; B29C 65/085; B29C 65/086; B29C 65/087; B29C 65/088; B29C 65/74; B29C 65/743; B29C 65/7435; B29C 65/7443; B29C 65/7455; B29C 66/344; B29C 65/02; B29C 65/4815

See application file for complete search history.

(56) References Cited

U.S. PATENT DOCUMENTS

| | | | |
|---|---|---|---|
| 9,867,740 B2* | 1/2018 | Zink | A61F 13/15699 |
| 2006/0270302 A1* | 11/2006 | Ando | A61F 13/4902 |
| | | | 442/328 |
| 2010/0076394 A1* | 3/2010 | Hayase | B29C 66/1122 |
| | | | 604/385.29 |
| 2016/0331600 A1* | 11/2016 | Polidori | B29C 66/83411 |

FOREIGN PATENT DOCUMENTS

| | | |
|---|---|---|
| JP | 2005-323780 A | 11/2005 |
| JP | 2008-104853 A | 5/2008 |
| JP | 2008-154998 A | 7/2008 |
| JP | 2009-56156 A | 3/2009 |
| JP | 2009-118986 A | 6/2009 |
| JP | 2009-297096 A | 12/2009 |
| JP | 2010-22588 A | 2/2010 |
| WO | WO-2009/074923 A2 | 6/2009 |

* cited by examiner

Rotational direction→

Rotational direction→

Rotational direction→

Rotational direction→

Rotational direction→

FIG. 16(a)
FIG. 16(d)
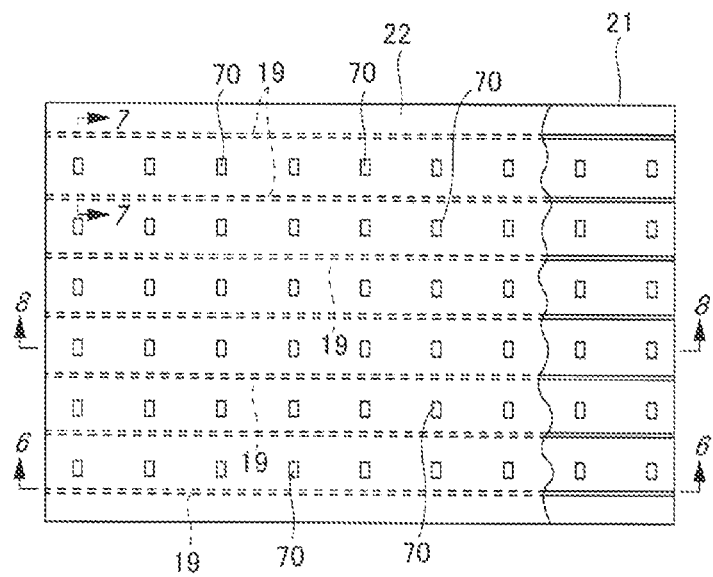
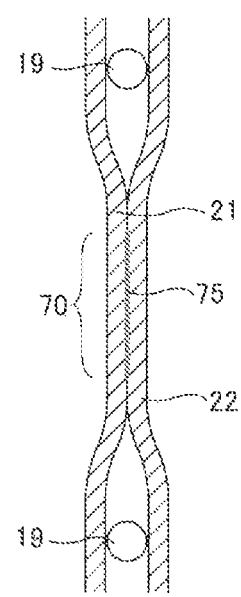
FIG. 16(b)
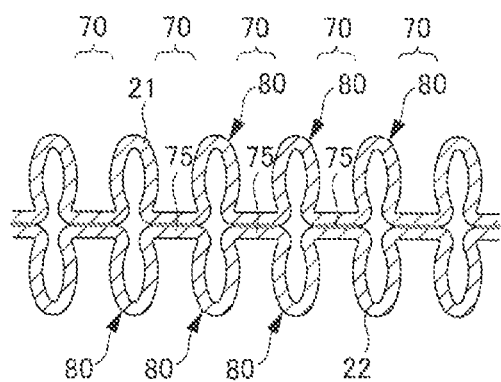
FIG. 16(c)
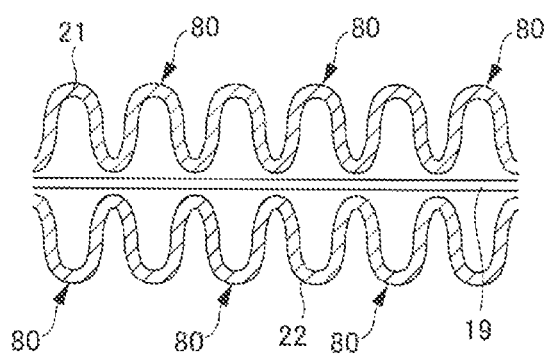

METHOD FOR FORMING STRETCHABLE STRUCTURE FOR ABSORBENT ARTICLE AND STRETCHABLE STRUCTURE FOR ABSORBENT ARTICLE

TECHNICAL FIELD

The present invention relates to a method for forming a stretchable structure for an absorbent article having elongated resilient and elastic members between stacking sheet layers, and the stretchable structure for the absorbent article capable of being manufactured by the manufacturing method.

BACKGROUND ART

For example, a pants-type disposable diaper includes an outer body having a front panel and a back panel, and an inner body that is fixed to the inner surface of the outer body and has an absorber. The front panel and the back panel of the outer body are joined together at the both sides to form a waist opening and a pair of right and left leg openings.

In the pants-type disposable diaper, elongated resilient and elastic members such as rubber threads are fixed in an extended state at several sections of the outer body along a circumferential direction to form a stretchable structure along the waist portion for improvement of the fit to the wearer's body. In particular, diapers including waist-portion resilient and elastic members at the edge portion of the waist opening along the width direction and lower waist portion resilient and elastic members closer to the crotch portion than the waist-portion resilient and elastic members along the width direction, are widely used due to their relatively good fit to the wearer's body.

Meanwhile, a tape-type disposable diaper has a crotch portion, a ventral-side portion extended to the front side of the crotch portion, a dorsal side portion extended to the back side of the crotch portion, an absorber provided in an area including the crotch portion, fastening tapes protruding from the both sides of the back portion, and target tapes positioned on the outer surface of the ventral-side portion to which the fastening tapes are to be fastened. To put the diaper on the wearer's body, the fastening tapes are turned from the both sides of the waist toward the outer surface of the ventral-side portion and are fastened to the target tapes. The tape-type disposable diapers are widely used for recipients of care (adults) as well as for infants. In general, the tape-type disposable diapers are inferior in the fit around the waist to the pants-type disposable diapers. To improve this, elongated resilient and elastic members such as rubber threads are fixed in the extended state to the dorsal side portion and the fastening tapes along the width direction to form a stretchable structure along the waist portion.

In addition, as an improvement of these stretchable structures, there has been proposed a stretchable structure in which two sheet layers 21 and 22 are intermittently joined together in an extending direction and a vertical direction orthogonal to the extending direction to form a large number of sheet joined sections 70, and a plurality of stretchable elongated resilient and elastic members 19 is arranged independently of the two sheet layers 21 and 22 so as not to pass through the sheet joined sections 70 between the sheet layers 21 and 22 (so as to pass through the non-joined sections) as illustrated in FIG. 16 (refer to Patent Document 1. The stretchable structure will be hereinafter also called vertical intermittent joined form). According to the related art, the vertical aligned sheet joined sections 70 form vertically continuous grooves, and the sections between the grooves form large pleats 80 that swell to the same degree on the both front and back sides. The grooves improve air permeability and the pleats 80 produce excellent fullness. Reference sign 75 in FIG. 16 represents welded portions of the sheet layers 21 and 22. However, even when the sheet joined sections 70 are formed by the use of an adhesive, pleats 80 have the same shape.

However, in the prior-art technology, the pleats make fluffy or wave-shaped pleats. Thus, there is a problem that the diaper is inferior in terms of appearance and air permeability.

Meanwhile, it is also known that two sheet layers are bonded intermittently in the extending direction and continuously in the direction crossing the extending direction to form a large number of sheet joined sections (refer to Patent Document 2, for example. Hereinafter also called vertical continuous joined form). In this form, the adhesion is made by a hot-melt adhesive or a welding process such as heat sealing or ultrasound sealing.

However, in such vertical continuous joined form, using a welding process for the sheet joined sections might cut the resilient and elastic members crossing the sheet joined sections.

CITATION LIST

Patent Document
  Patent Document 1: JP-A No. 2009-297096
  Patent Document 2: JP-A No. 2010-22588

SUMMARY OF INVENTION

Technical Problem

A major object of the present invention is to prevent cutting of the resilient and elastic members by a welding process.

Solution to Problem

The inventor of the present invention has earnestly studied a solution to the foregoing problem and found that the resilient and elastic members were cut mainly by excessive pressurization rather than by heating, and that the pressure by which to allow appropriate welding at sections without the resilient and elastic members was too high on the resilient and elastic members. The present invention is based on the findings.

A method for forming a stretchable structure for an absorbent article, including, while rotating a first roll with joint convex parts provided at circumferential intervals on an outer peripheral surface and a second roll opposed to the first roll in opposite directions around axis centers thereof, passing a first sheet layer, a second sheet layer, and elongated resilient and elastic members continuously disposed in an MD direction between the two sheet layers, between the first roll and the second roll, and pressurizing and heating the first sheet layer and the second sheet layer sandwiched between the joint convex parts of the first roll and the second roll to form sheet joined sections by welding the first sheet layer and the second sheet layer in such a manner as to cross the resilient and elastic members and have MD-direction intervals therebetween, wherein circumferentially continuous grooves are formed on a pressurization surface for the pressurization of at least one of the first roll and the second roll in at least partial ranges of rotation periods of the first roll and the second roll, and at the time of the pressurization and heating, passage sections of the resilient and elastic members are pressurized and heated in positions including the grooves and non-passage sections of the resilient and elastic members are pressurized and heated in positions not including the grooves.

(Operation and Effect)

In this manner in which the circumferentially continuous grooves are formed on the pressurization surface of at least one of the first roll and the second roll, at the time of formation of the sheet joined sections, the passage sections of the elongated resilient and elastic members are pressurized and heated in the positions including the grooves and the non-passage sections of the resilient and elastic members are pressurized and heated in the positions not including the grooves, and the difference between pressure applied to the first sheet layer and the second sheet layer in the non-passage sections of the resilient and elastic members and pressure applied to the first sheet layer, the resilient and elastic members, and the second sheet layer in the passage sections of the resilient and elastic members becomes smaller. This reduces the pressure applied to the resilient and elastic members, while decreasing variations in welding quality, thereby making the cutting of the resilient and elastic members less to occur.

The method for forming a stretchable structure for an absorbent article, wherein the joint convex parts are elongated and extended in a direction crossing the resilient and elastic members and have first portions relatively long in a circumferential direction and second portions relatively short in the circumferential direction, and the first portions are positioned in sections including the passage sections of the resilient and elastic members, and the second portions are positioned in sections not including the passage sections of the resilient and elastic members.

(Operation and Effect)

By forming the joint convex parts in such a shape as described above, it is possible to further decrease the pressure applied to the passage sections of the resilient and elastic members, thereby further enhancing the effect of cutting prevention. The same effect could be produced by making the grooves deeper, but in this case, the pressurization and heating of the passage sections of the resilient and elastic members would be likely to be insufficient. Accordingly, the shape of the joint convex parts is changed in a preferred mode.

The method for forming a stretchable structure for an absorbent article, wherein the joint convex parts are elongated and extended in a direction crossing the resilient and elastic members and have protrusion parts protruding from CD-direction both sides of sections crossing the resilient and elastic members in a rotational direction.

(Operation and Effect)

By forming the joint convex parts in such a shape as described above, the resilient and elastic members are guided to a space between the protrusion parts, thereby preferably allowing the passage sections of the resilient and elastic members to be reliably positioned in the positions including the grooves.

The method for forming a stretchable structure for an absorbent article, wherein the grooves are formed in partial ranges of rotation periods of the first roll and the second roll but no groove is formed in the other ranges, and the resilient and elastic members are cut by the pressurization and heating in the ranges without the grooves and the resilient and elastic members are not cut in the ranges with the grooves at the time of the pressurization and heating.

(Operation and Effect)

In the disposable diaper, the resilient and elastic members need to be passed through some regions such as a region overlapping the absorber due to a manufactural reason, but the elasticity of the resilient and elastic members is unnecessary in these regions and the resilient and elastic members are finely cut in the regions to make their elasticity disable. The present invention is intended to prevent the resilient and elastic members from being cut at the time of welding the first sheet layer and the second sheet layer by the use of the grooves on the pressurization surface. However, the grooves are not provided on the pressurization surface in the region without the need for elasticity such that the welding process is also used for cutting the resilient and elastic members. This allows the formation of the sheet joined sections and the cutting of the resilient and elastic members at the same time, thereby simplifying the manufacturing process.

A stretchable structure for an absorbent article including: a first sheet layer; a second sheet layer opposed to one surface of the first sheet layer; and a plurality of elongated resilient and elastic members provided between the first sheet layer and the second sheet layer along an extending direction at intervals therebetween, wherein the first sheet layer and the second sheet layer are joined together by a welding process that is intermittent in the extending direction and continuous in a direction crossing the extending direction to form sheet joined sections, the resilient and elastic members are fixed to the first sheet layer and the second sheet layer by the welding process for forming the sheet joined sections in positions crossing the sheet joined sections, portions of the first sheet layer and the second sheet layer between the sheet joined sections swell in opposite directions to form pleats when the first sheet layer and the second sheet layer are contracted along with contraction of the resilient and elastic members, and in one of the first sheet layer and the second sheet layer at the sheet joined sections in a natural length state, an apparent thickness of the portions overlapping centers of the resilient and elastic members is 80 to 100% of an apparent thickness of the portions without the resilient and elastic members.

(Operation and Effect)

The present invention is based on the vertical continuous joined form and is structured such that, in one of the first sheet layer and the second sheet layer at the sheet joined sections in the natural length state, the difference between the apparent thickness of the portions overlapping the centers of the resilient and elastic members and the apparent thickness of the portions without the resilient and elastic members is small. In the sheet layer with the smaller thickness difference, the portions covering the resilient and elastic members are thicker than conventional ones. This provides a cushioning texture and makes the resilient and elastic members softer. The same results can be obtained even when the sheet is stretched to some extent during use.

The foregoing structure can be formed by the method as discussed hereinbefore. The sheet layer in contact with the grooves enters into the grooves at the time of the pressurization and heating, the sheet layer with the resilient and elastic members becomes longer in the direction crossing the resilient and elastic members, and the thickness difference in the sheet layer becomes small both in the natural length state and the worn state.

According to conventional manufacturing methods, both the first sheet layer and the second sheet layer are flat in the direction crossing the resilient and elastic members at the time of welding the sheet joined sections, and the resilient and elastic members become larger in diameter in the natural length state and the worn state than at the time of manufacture. Accordingly, the first sheet layer and the second sheet layer are stretched and thinned at the sections with the resilient and elastic members to make the difference in the apparent thickness larger.

In the present invention, the mode in which the welding process for forming the sheet joined sections is continuous means the mode in which the first sheet layer and the resilient and elastic members are welded and the second sheet layer and the resilient and elastic members are welded, and thus the first sheet layer and the second sheet layer are welded indirectly to make the welding continuous.

In addition, the mode in which the resilient and elastic members are fixed to the sheet layers by the welding process in the positions crossing the sheet joined sections includes the mode in which the welding is reinforced by another means such as an adhesive in the positions crossing the sheet joined sections or other positions.

Further, the apparent thickness is measured in such a manner that the sheet joined sections are cut in the direction orthogonal to the resilient and elastic members under conditions in conformity with JIS L 1913: 2010, the cut section is photographed with a magnification of 100 times by a microscope, and the thickness is visually measured with a ruler from the photograph.

The stretchable structure for an absorbent article, wherein the sheet joined sections are elongated and extended in a direction crossing the resilient and elastic members and have first portions relatively long in a width direction and second portions relatively short in the width direction, and the first portions are positioned in sections including passage sections of the resilient and elastic members, and the second portions are positioned in sections not including the passage sections of the resilient and elastic members.

(Operation and Effect)

The stretchable structure can be formed by the method as discussed hereinbefore.

The stretchable structure for an absorbent article, wherein the sheet joined sections are elongated and extended in a direction crossing the resilient and elastic members, and have, in sections crossing the resilient and elastic members, protrusion parts that protrude from both sides in the direction crossing the resilient and elastic members to one side in the width-direction.

(Operation and Effect)

The stretchable structure can be formed by the method as discussed hereinbefore.

The stretchable structure for an absorbent article, wherein the absorbent article is a pants-type disposable diaper including an outer body constituting a front panel and a back panel and an inner body that is fixed to an inner surface of the outer body and includes an absorber, the front panel of the outer body and the back panel of the outer body being joined together at both sides to form side seal portions, thereby forming a waist portion in an annular shape, a waist opening portion, and a pair of right and left leg openings, and the stretchable structure is provided in a region of the outer body including at least width-direction both sides of the inner body such that the resilient and elastic members are arranged in the width direction.

(Operation and Effect)

The stretchable structure of the present invention is preferably suited to the region of the outer body in the pants-type disposable diaper positioned on the width-direction both sides of the inner body.

Advantageous Effects of Invention

As described above, according to the present invention, it is possible to provide the advantages of allowing appropriate welding, and making the cutting of the resilient and elastic members less prone to occur, and the like.

BRIEF DESCRIPTION OF THE DRAWINGS

FIG. 16(a) is a plane view of a conventional stretchable structure in the opened state, FIG. 16(b) is a cross-sectional view of the same in the natural length state taken along line 8-8, FIG. 16(c) is a cross-sectional view of the same in the natural length state taken along line 6-6, and FIG. 16(d) is a cross-sectional view of the same taken along line 7-7.

DESCRIPTION OF EMBODIMENTS

Embodiments of the present invention will be descried below in detail with reference to the accompanying drawings.

<About a Stretchable Structure>

FIGS. 1 to 8 illustrate a pants-type disposable diaper 100 as one example of pants-type disposable diapers. The pants-type disposable diaper 100 is composed of an outer body 12 constituting the outer surface (back surface) of the product and an inner body 200 stuck to the inner surface of the outer body 12. Reference sign Y represents the entire length of the diaper, and reference sign X represents the entire width of the diaper.

The inner body 200 is a part absorbing and retaining an excretion such as urine, and the outer body 12 is a part to be attached to the wearer's body. The dotted portions in the cross-sectional views indicate joined sections where constituent members are joined together. The joined sections are formed by application of a hot-melt adhesive or the like in a solid, bead, curtain, summit, or spiral pattern. In the following description, the "front-back direction" refers to the direction linking the ventral side (front side) and the dorsal side (rear side), and the "width direction" refers to the direction (right-left direction) orthogonal to the front-back direction. The "up-down direction" refers to the direction that becomes orthogonal to the waist direction when the diaper 100 is worn, that is, when the diaper 100 is folded into two at the crotch portion such that the front panel and the back panel are overlapped at the both sides, in other words, the direction linking a waist opening WO and a crotch portion.

(Inner Body)

Figure 3:
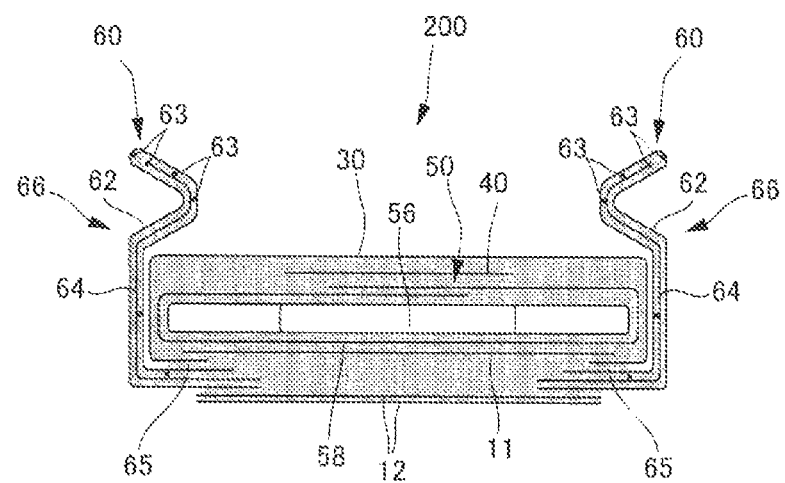
FIG. 3 is a cross-sectional view of FIG. 1 taken along line 3-3.
Figure 4:
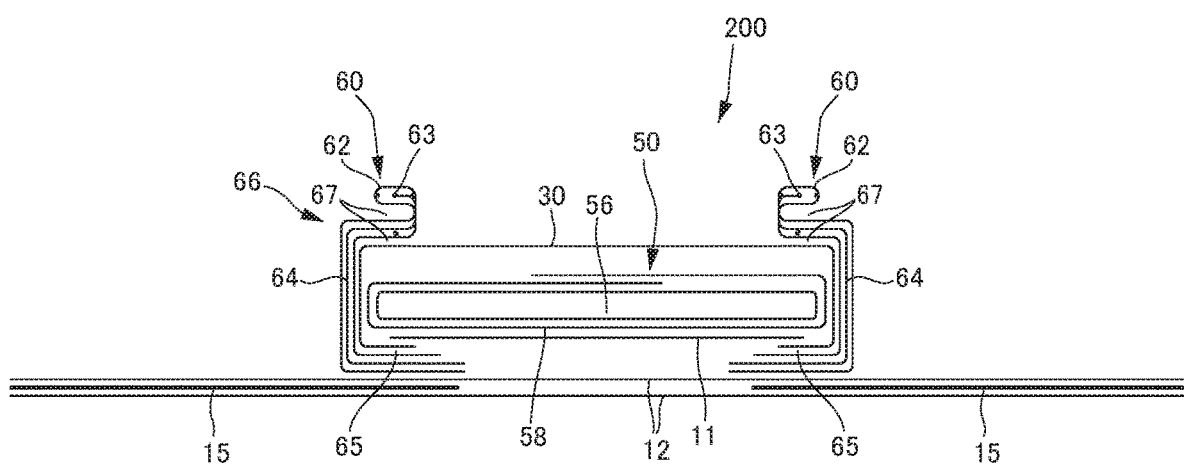
FIG. 4 is a cross-sectional view of FIG. 1 taken along line 4-4.
Figure 5:
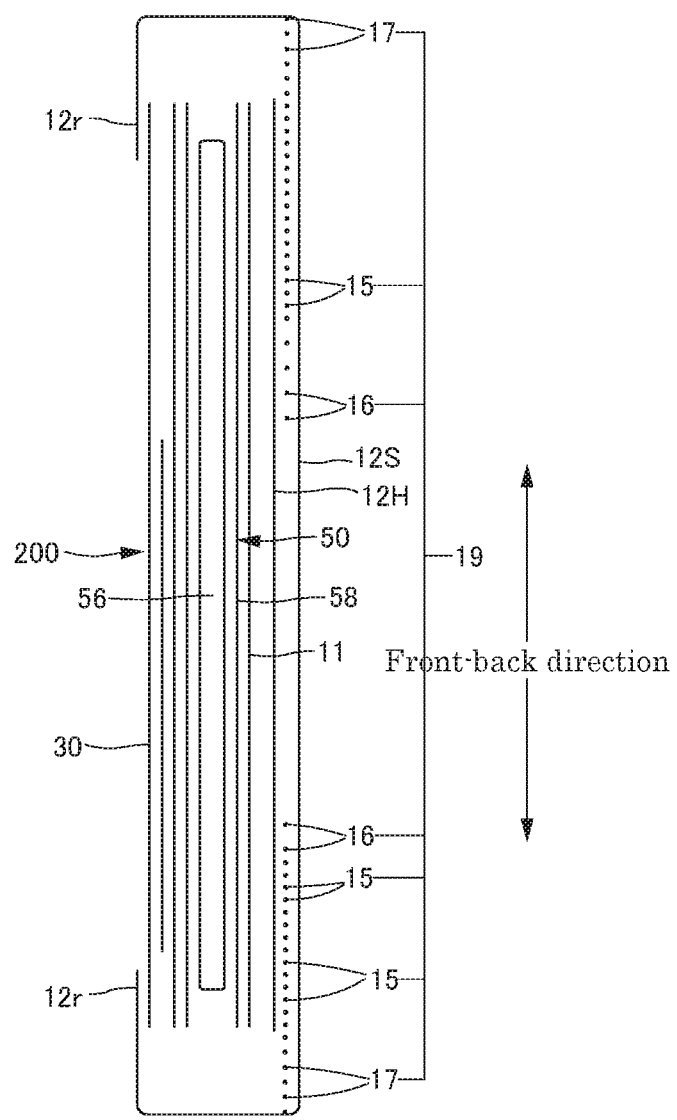
FIG. 5 is a cross-sectional view of FIG. 1 taken along line 5-5.
Figure 6A:
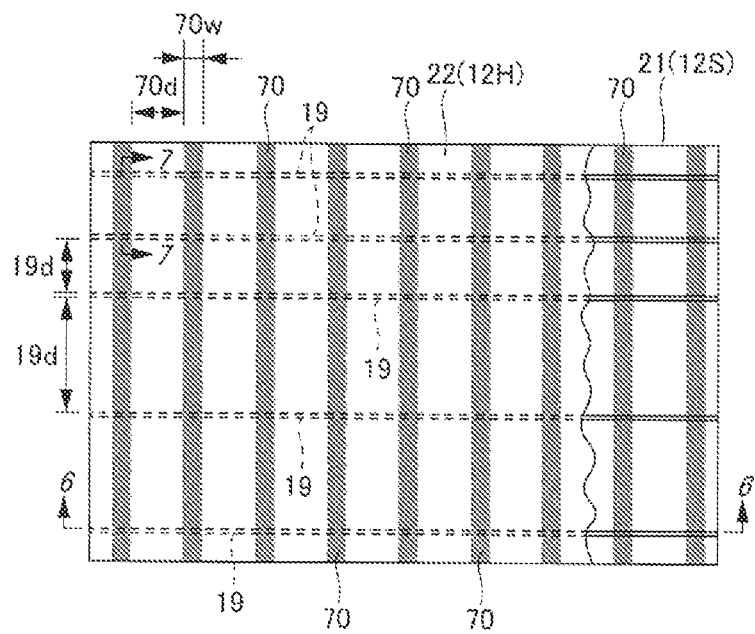
FIG. 6(a) is a plane view of a stretchable structure in an opened state.
Figure 6D:
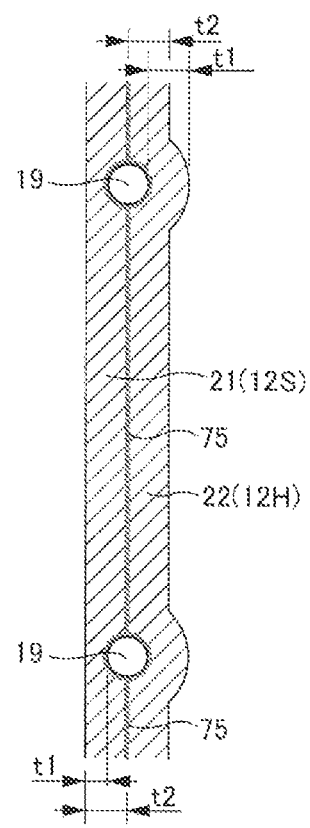
FIG. 6(d) is a cross-sectional view of the same taken along line 7-7.
Figure 6B:
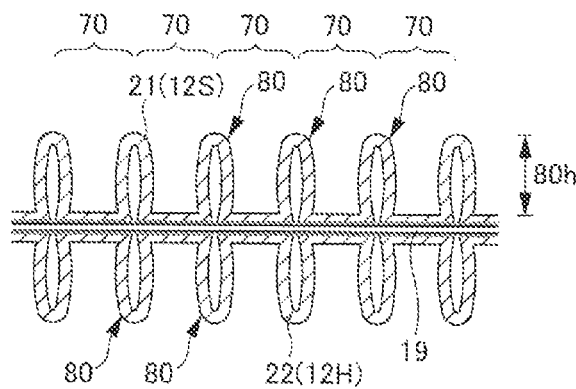
FIG. 6(b) is a cross-sectional view of the same in a natural length state taken along line 6-6.
Figure 6C:
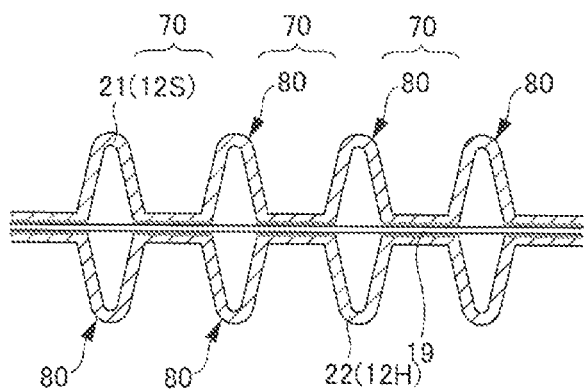
FIG. 6(c) is a cross-sectional view of the same in a state stretched to some extent taken along line 6-6.

The inner body 200 is rectangular in the illustrated example but may have an arbitrary shape. As illustrated in FIGS. 3 to 5, the inner body 200 is a main panel that performs an absorption function and includes a top sheet 30 on the body side, a liquid impervious sheet 11, and an absorbent element 50 intervening between the top sheet 30 and the liquid impervious sheet 11. Reference sign 40 represents an interlayer sheet (second sheet) that is interposed between the top sheet 30 and the absorbent element 50 to move a liquid having passed through the top sheet 30 quickly to the absorbent element 50. Reference sign 60 represents three-dimensional gathers 60 that are provided on the both sides of the inner body 200 and stand toward the wearer's body to prevent excretion from leaking to the both sides of the inner body 200.

(Top Sheet)

The top sheet 30 is pervious to liquid and may be a porous or non-porous non-woven fabric sheet or a porous plastic sheet, for example. There is no particular limitation on raw fibers for the non-woven fabric. For example, the raw fibers may be synthetic fibers based on olefin such as polyethylene or polypropylene, polyester, or polyamide, reproduced fibers of rayon, cupra, or the like, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle punching, air-through processing, and point bonding, for example. For flexibility and drape properties, spun-bonding and spun-lacing methods are preferred. For bulkiness and softness, air-through processing, point-bonding, and thermal bonding methods are preferred.

The top sheet 30 may be composed of a single sheet or a layered sheet obtained by sticking two or more sheets each other. Similarly, the top sheet 30 may be composed of a single sheet or two or more sheets in a planar direction.

In the case of providing the three-dimensional gathers 60, it is preferred that the both sides of the top sheet 30 are extended up to the back side of the absorbent element 50 through the liquid impervious sheet 11 and the three-dimensional gathers 60, and are bonded to the liquid impervious sheet 11 and the three-dimensional gathers 60 by a hot-melt adhesive or the like to prevent liquid penetration.

(Interlayer Sheet)

To move the liquid having passed through the top sheet 30 quickly to the absorber, the interlayer sheet (called also "second sheet") 40 higher in liquid permission speed than the top sheet 30 may be provided. The interlayer sheet 40 can move the liquid quickly to the absorber with enhancement in absorption performance of the absorber and also can prevent a "reflowing" phenomenon of the absorbed liquid from the absorber to keep the top sheet 30 in a dry state. The interlayer sheet 40 may not be provided.

The material for the interlayer sheet 40 may be the same material as that for the top sheet 30, a spun-laced, spun-bonded, SMS, or pulp non-woven fabric sheet, a sheet of mixture of pulp and rayon, point-bonded paper, or crepe paper, for example. In particular, the air-through non-woven fabric is preferred for its bulkiness. Core-sheath composite fibers are preferably used for the air-through non-woven fabric. The resin for use in the core may be polypropylene (PP) but is preferably polyester (PET) for its high rigidity. The basis weight is preferably 20 to 80 $g/m^2$, more preferably 25 to 60 $g/m^2$. The thickness of the raw fibers in the non-woven fabric is preferably 2.2 to 10 dtex. To make the non-woven fabric high in bulkiness, eccentric fibers with no core in the center, hollow fibers, or eccentric and hollow fibers are preferably used for some or all of the raw fibers.

In the illustrated mode, the interlayer sheet 40 is shorter than the width of an absorber 56 and arranged in the center of the absorber 56. Alternatively, the interlayer sheet 40 may be provided over the entire width of the absorber 56. The longitudinal length of the interlayer sheet 40 may be the same as the length of the absorber 56 or may fall within a shorter-length range centered on the area for receiving the liquid.

(Liquid Impervious Sheet)

There is no particular limitation on the material for the liquid impervious sheet 11. For example, the liquid impervious sheet 11 may be formed from a plastic film made of an olefin resin such as polyethylene or polypropylene, a laminate non-woven fabric sheet in which a plastic film is provided on the surface of non-woven fabric, or a laminate sheet in which non-woven fabric or the like is laid on and joined to a plastic film. The liquid impervious sheet 11 is preferably formed from a liquid impervious and moisture-pervious material having been used preferably in recent years from the viewpoint of stuffiness prevention. As the moisture-pervious plastic film, there has been widely used a microporous plastic film that is obtained by melting and kneading an inorganic filling agent in an olefin resin such as polyethylene or polypropylene to form a sheet and then elongating the sheet in a uniaxial or biaxial direction. Besides, the liquid impervious sheet 11 may be a non-woven fabric sheet of microdenier fibers, or may be a liquid impervious sheet that is formed, without the use of a plastic film, by enhancing leak-preventive performance by reducing the size of air gaps between fibers with the application of heat or pressure or by coating the sheet with a high-water absorption resin, a hydrophobic resin, or a water repellent agent.

It is preferable that for enhancement of leak-preventive performance, the liquid impervious sheet 11 may be extended through the both sides of the absorbent element 50 to the both sides of the absorbent element 50 on the top sheet 30 side. The appropriate width of the extended portion is about 5 to 20 mm on each of the right and left sides.

An excretion indicator changed in color by absorption of a liquid may be provided on the inside of the liquid impervious sheet 11, in particular, on the side surfaces of the absorber 56.

(Three-Dimensional Gathers)

The three-dimensional gathers 60 are belt-like members extended entirely along the both sides of the inner body 200 in the front-back direction. The three-dimensional gathers 60 are provided to shut off urine or loose stool moving laterally over the top sheet 30 to prevent lateral leakage of the liquid. In this embodiment, the three-dimensional gathers 60 stand on the sides of the inner body 200. The three-dimensional gathers 60 stand obliquely toward the width-direction central portion at the base-side portions, and stand obliquely toward the width-direction outside at the middle to tip portions.

More specifically, the three-dimensional gathers 60 are formed such that belt-like gather sheets 62 having the same length as the front-back length of the inner body 200 are folded back in two in the width direction, and a plurality of elongated resilient and elastic members 63 is fixed in the extended state along the longitudinal direction at width-direction intervals between the sheets at the folded parts and their neighborhoods. The ends of the three-dimensional gathers 60 opposite to the folded parts in the width direction constitute attachment parts 65 fixed to the back surface of the inner body 200 at the side edge. The parts of the three-dimensional gathers 60 other than the attachment parts 65 constitute protrusion parts 66 (folded-side parts) that protrude from the attachment parts 65. The front-back both ends of the protrusion parts 66 are composed of base-side portions that extend from the attachment parts 65 through the sides of the inner body 200 to the side surface of the top sheet 30 and are fixed as front-back fixed portions 67 to the side surfaces of the top sheet 30 by a hot-melt adhesive or heat seal, and tip-side portions that are folded outward in the width direction from the tips of the base-side portions and fixed to the base-side portions. The front-back intermediate portions of the protrusion parts are non-fixed free portions (inner free portions). The elongated resilient and elastic members 63 are fixed to the free portions in the extended state along front-back direction.

The gather sheets 62 may be preferably formed by applying a water repellent treatment with silicon or the like as necessary to flexible non-woven fabric excellent in uniformity and concealing performance such as spun-bonded non-woven fabric (SS, SSS, or the like), SMS non-woven fabric (SMS, SSMMS, or the like), or melt-blown non-woven fabric. The basis weight of the fibers is preferably about 10 to 30 g/m². The elongated resilient and elastic members 63 may be rubber threads or the like. In the case of using spandex rubber threads, the thickness of the threads is preferably 470 to 1240 dtex, more specifically 620 to 940 dtex. The extension ratio of the threads at the time of fixing is preferably 150 to 350%, more specifically 200 to 300%. The "extension ratio" herein takes on a value relative to the natural length as 100%. In addition, a water-proof film 64 may intervene in the gather sheet folded in two as illustrated in the drawing.

The number of the elongated resilient and elastic members 63 provided on the free portions of the three-dimensional gathers 60 is preferably two to six, more specifically three to five. An arrangement interval 60$d$ is appropriately 3 to 10 mm. According to this configuration, the diaper is likely to touch the skin by surface with the elongated resilient and elastic members 63. The elongated resilient and elastic members 63 may be arranged not only at the tip-side portions but also at the base-side portions.

The attachment parts 65 of the three-dimensional gathers 60 may be fixed to an appropriate member such as the top sheet 30, the liquid impervious sheet 11, or the absorbent element 50 in the inner body 200.

In the thus configured three-dimensional gathers 60, the contraction force of the elongated resilient and elastic members 63 acts to make the both front-back end portions closer to each other. The protrusion parts 66 are fixed such the both front-back end portions do not stand, whereas the intermediate portions between the protrusion parts 66 are non-fixed free portions. Accordingly, only the free portions stand to touch the wearer's body as illustrated in FIG. 3. In particular, when the attachment parts 65 are positioned on the back surface of the inner body 200, the three-dimensional gathers 60 stand and open outward in the width direction at the crotch portion and its neighborhood. Accordingly, the three-dimensional gathers 60 are brought into surface contact with the circumferences of the legs to produce an improved fit.

Figure 7:
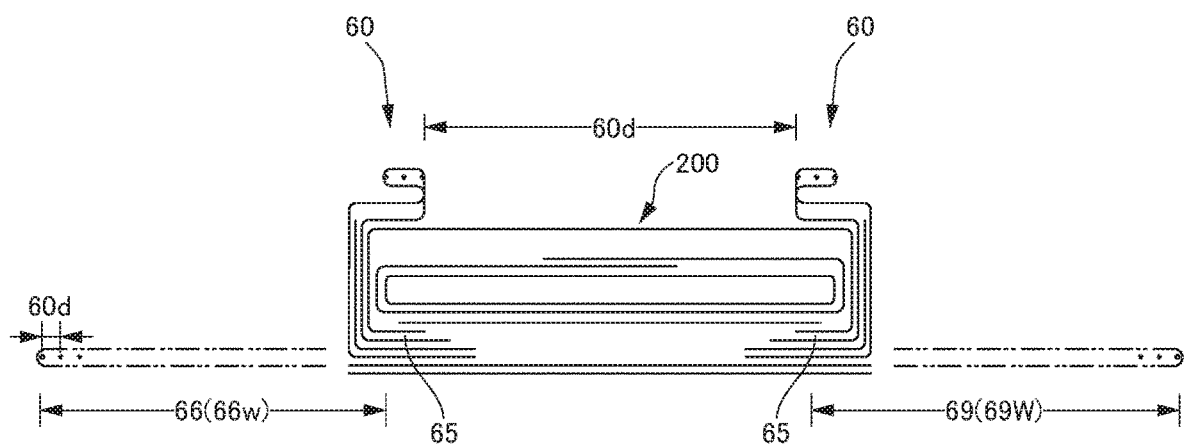
FIG. 7 is a cross-sectional view of main components of the pants-type disposable diaper.

The dimensions of the three-dimensional gathers 60 can be decided as appropriate. In the case of a disposable diaper for infants, a standing height (width of the protrusion parts 66 in the open state) 66$w$ of the three-dimensional gathers 60 is preferably 15 to 60 mm, more preferably 20 to 40 mm as illustrated in FIG. 7, for example. In addition, when the three-dimensional gathers 60 are flatly folded in parallel to the surface of the top sheet 30, a separation distance 60$d$ between folds on the innermost side is preferably 60 to 190 mm, more preferably 70 to 140 mm.

Unlike in the illustrated example, the three-dimensional gathers may be provided doubly (in two rows) on each of the right and left sides of the inner body 200.

(Absorbent Element)

The absorbent element 50 has the absorber 56 and a wrapping sheet 58 for wrapping the entire absorber 56. The wrapping sheet 58 may not be provided.

(Absorber)

The absorber 56 can be formed from a fiber assembly. The fiber assembly may be accumulated short fibers such as fluff pulp or synthetic fibers or a filament assembly obtained by opening tows (fiber bundles) of synthetic fibers such as cellulose acetate as necessary. The basis weight of the fluffy pulp or accumulated short fibers may be about 100 to 300 g/m², and the basis weight of the filament assembly may be about 30 to 120 g/m², for example. The fineness of synthetic fibers is 1 to 16 dtex, preferably 1 to 10 dtex, more preferably 1 to 5 dtex, for example. In the case of the filament assembly, the filaments may be non-crimped fibers but are preferably crimped fibers. The number of crimps in the crimped fibers may be about 5 to 75 per inch, preferably 10 to 50 per inch, more preferably about 15 to 50 per inch, for example. The crimped fibers are evenly crimped in many cases. High-absorbent polymer particles are preferably dispersed and held in the absorber 56.

The absorber 56 may be rectangular in shape but preferably has an hourglass shape with a front end portion, a back end portion, and a narrower portion that is positioned between the front and back end portions and is narrower than the two end portions as illustrated in FIG. 6 to improve the fit of the absorber 56 and the three-dimensional gathers 60 to the circumferences of the legs.

The dimensions of the absorber can be decided as appropriate. Nevertheless, the absorber preferably extends to the peripheral edges or their neighborhoods of the inner body in the front-back direction and the width direction. Reference sign 56X represents the width of the absorber 56.

(High-Absorbent Polymer Particles)

The absorber 56 may partially or entirely contain high-absorbent polymer particles. The high-absorbent polymer particles include "powder" as well as "particles". The high-absorbent polymer particles may be particles to be generally used in this type of absorbent article and the particle size is preferably 1000 μm or less, more preferably 150 to 400 μm.

There is no particular limitation on the material for the high-absorbent polymer particles but the material preferably has a water absorption capacity of 40 g/g or more. The high-absorbent polymer particles may be based on starch, cellulose, or synthetic polymer. The high-absorbent polymer particles may be made of a starch-acrylate graft copolymer, a saponified substance of starch-acrylonitrile copolymer, a crosslinking substance of carboxymethyl-cellulose sodium, an acrylate polymer, or the like. The high-absorbent polymer particles are preferably used in a general particulate form but may be used in another form.

The water absorption rate of the high-absorbent polymer particles is preferably 40 seconds or less. When a water absorption rate exceeds 40 seconds, the absorbed liquid is more likely to flow back from the absorber 56 to the outside.

The basis weight of the high-absorbent polymer particles can be decided as appropriate according to the absorbing capability required for the use of the absorber 56. Although not definitely specified, the basis weight may be 50 to 350 g/m$^2$. When the basis weight of the polymer is less than 50 g/m$^2$, it is difficult to provide the necessary absorbing capability. When the basis weight of the polymer exceeds 350 g/m$^2$, the absorbing effect becomes saturated.

If necessary, the high-absorbent polymer particles can be adjusted in dispersing density or dispersing quantity along the planar direction of the absorber 56. For example, the dispersing quantity of the high-absorbent polymer particles may be larger in the excretion area than the other areas. With regard to gender differences, the dispersing density (quantity) of the high-absorbent polymer particles may be increased at the front side of the product for male, and may be increased at the central portion of the product for female. In addition, the polymer may not be provided locally (in spots, for example) in the planar direction of the absorber 56.

(Wrapping Sheet)

The material for the wrapping sheet 58 may be tissue paper, in particular, crepe paper, non-woven fabric, polyethylene-laminated non-woven fabric, a porous sheet, or the like. However, the material sheet is desirably configured to retain the high-absorbent polymer particles. In the case of using non-woven fabric instead of crepe paper, the hydrophilic SMS non-woven fabric (SMS, SSMMS, or the like) is preferred in particular and its material may be polypropylene, polyethylene/polypropylene composite, or the like. The basis weight of the material is desirably 5 to 40 g/m$^2$, in particular 10 to 30 g/m$^2$.

The form of wrapping by the wrapping sheet 58 can be decided as appropriate. Nevertheless, from the viewpoint of ease of manufacture and prevention of leakage of the high-absorbent polymer particles from the front and back end edges, the wrapping sheet 58 preferably wraps the absorber 56 in a cylindrical form to surround the front and back surfaces and both side surfaces of the absorber 56, and has front and back end portions extended off from the front and back sides of the absorber 56 so that the extended portions are crushed on the top and bottom sides and joined together by a joining means such as a hot-melt adhesive.

(Outer Body)

Figure 8:
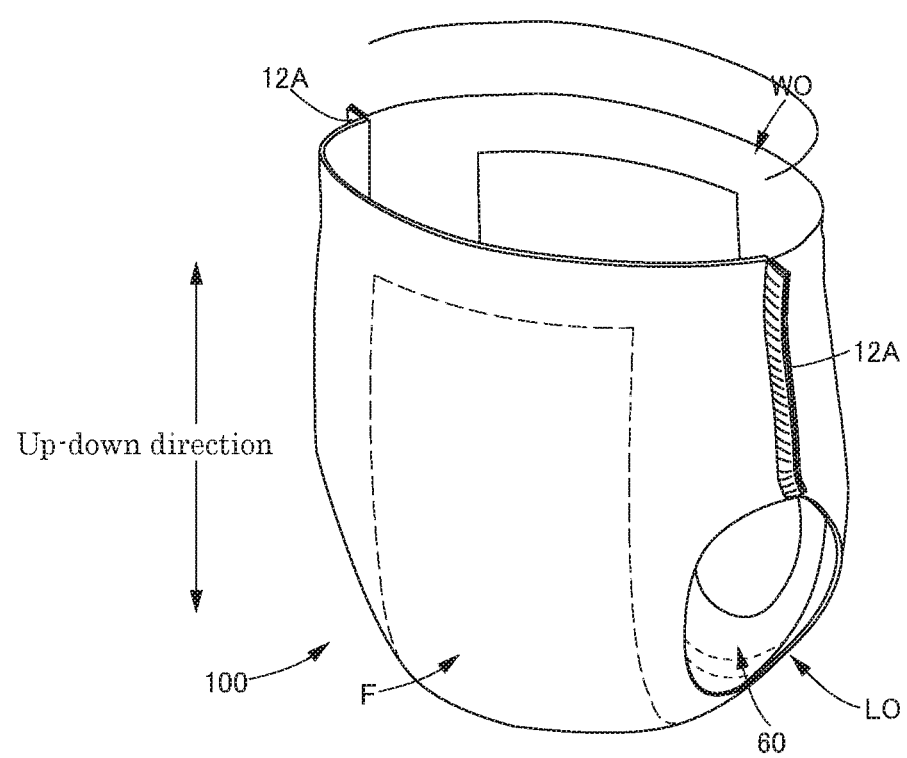
FIG. 8 is a perspective view of the pants-type disposable diaper.

The outer body 12 has a part constituting a front panel F extended from the crotch portion to the ventral side and a part constituting a back panel B extended from the crotch portion to the dorsal side. The front panel F and the back panel B are joined together at the both sides to form a waist opening WO through which the wearer's waist is passed and a pair of right and left leg openings LO through which the wearer's legs are passed as illustrated in FIG. 8. Reference sign 12A represents joined portions (hereinafter, also called side seal portions). The crotch portion refers to a central portion in the front-back direction from the waist edge of the front panel F to the waist edge of the back panel B in the opened state. The parts on the front side and the back side of the crotch portion refer to the front panel F and the back panel B, respectively.

The outer body 12 has a waist portion T determined as a front-back range from the waist opening WO to the upper ends of the leg openings LO, and an intermediate portion L determined as a front-back range forming the leg openings LO (between the front-back area having the side seal portions 12A of the front panel F and the front-back area having the side seal portions 12A of the back panel B). The waist portion T is conceptually divided into a "waist portion" W forming the edge of the waist opening and a "lower waist portion" U as a portion under the waist portion W. In general, when there are boundaries in the waist portion T with changes in width-direction expansion and contraction stress (for example, changes in the thickness or extension ratio of the resilient and elastic members), the part nearer the waist opening WO than the boundary nearest the waist opening WO constitutes the waist portion W. When there are no boundaries, the part nearer the waist opening WO than the absorber 56 or the inner body 200 constitutes the waist portion W. The lengths of these parts vary depending on the size of the product and can be decided as appropriate. As an example, the length of the waist edge portion W may be 15 to 40 mm, and the length of the lower waist portion U may be 65 to 120 mm. The both ends of the intermediate portion L are narrowed along the circumferences of the wearer's legs, and the wearer's legs are placed through the narrowed ends. As a result, the outer body 12 has an almost hourglass shape as a whole. The degree of narrowing of the outer body 12 can be decided as appropriate. As in the mode illustrated in FIGS. 1 to 8, the outer body 12 is preferably narrower than the inner body 200 at the narrowest area for simple appearance. Alternatively, the outer body 12 may be wider than the inner body 200 even at the narrowest area.

The outer body 12 is formed by bonding two sheet materials 12S and 12H as illustrated in FIGS. 3 to 6. The second sheet material 12H positioned inside extends up to the edge of the waist opening WO, whereas the first sheet material 12S positioned outside wraps around the edge of the second sheet material 12H on the waist side and folds back toward the inside. Folded parts 12r are extended to cover the upper end portion of the inner body 200 on the waist side.

There is no particular limitation on the sheet materials 12S and 12H as far as they are sheet material, but they are preferably formed from non-woven fabric. There is no specific limitation on raw fibers for the non-woven fabric. For example, the raw fibers may be synthetic fibers based on olefin such as polyethylene or polypropylene, polyester, or polyamide, reproduced fibers of rayon, cupra, or the like, natural fibers of cotton or the like, or mixed fibers or composite fibers of two or more of the foregoing fibers. The non-woven fabric may be produced by any processing method. The processing method may be any of publicly known methods such as spun-lacing, spun-bonding, thermal bonding, melt-blowing, needle-punching, air-through processing, and point-bonding, for example.

The outer body 12 has elongated resilient and elastic members 19 such as rubber threads (waist portion resilient and elastic members 17, lower waist portion resilient and elastic members 15, and intermediate portion resilient and elastic members 16) provided at a predetermined extension ratio between the sheet materials 12S and 12H to enhance the fit to the wearer's waist. The elongated resilient and elastic members 19 may be formed from a synthetic rubber or a natural rubber.

More specifically, in the waist portions W of the back panel B and the front panel F, a plurality of waist portion resilient and elastic members 17 is fixed in an extended state along the width direction at a predetermined extension ratio with up-down intervals in such a manner as to be entirely continuous in the width direction, between the inner surface of the second sheet material 12H and the outer surfaces of the folded parts 12r of the first sheet material 12S. One or more of the waist portion resilient and elastic members 17 in the area adjacent to the lower waist portion U may overlap the inner body 200 or may be provided on the both sides of the central portion in the width direction with the exception of the central portion in the width direction overlapping the inner body 200. As the waist portion resilient and elastic members 17, about 3 to 22 rubber threads with a thickness of about 155 to 1880 dtex, in particular about 470 to 1240 dtex (this is applied to a synthetic rubber, and in the case of a natural rubber, a cross-section area of about 0.05 to 1.5 mm$^2$, in particular about 0.1 to 1.0 mm$^2$) are preferably fixed at an extension ratio of about 150 to 400%, in particular about 220 to 320%, and at intervals of 4 to 12 mm. All of the waist portion resilient and elastic members 17 may not be equal in thickness and extension ratio. For example, the resilient and elastic members may be different in thickness and extension ratio between the upper and lower sides of the waist portion W.

In the lower waist portions U of the front panel F and the back panel B, a plurality of lower waist portion resilient and elastic members 15 composed of elongated resilient and elastic members is fixed in an extended state along the width direction at a predetermined extension ratio with up-down intervals in such a manner as to be entirely continuous in the width direction, between the outer surface of the second sheet material 12H and the inner surface of the first sheet material 12S on the upper side and both sides of the central portion in the width direction with the exception of the central portion in the width direction overlapping the inner body 200.

As the lower waist portion resilient and elastic members 15, about 5 to 30 rubber threads with a thickness of 155 to 1880 dtex, in particular about 470 to 1240 dtex (this is applied to a synthetic rubber, and in the case of a natural rubber, a cross-section area of about 0.05 to 1.5 mm$^2$, in particular about 0.1 to 1.0 mm$^2$) are preferably fixed at an extension ratio of about 200 to 350%, in particular about 240 to 300%, and at intervals of 1 to 15 mm, in particular 3 to 8 mm.

In the intermediate portions L of the front panel F and the back panel B, a plurality of intermediate portion resilient and elastic members 16 composed of elongated resilient and elastic members is fixed in an extended state along the width direction at a predetermined extension ratio with up-down intervals in such a manner as to be entirely continuous in the width direction between the outer surface of the second sheet material 12H and the inner surface of the first sheet material 12S on the both sides of the central portion in the width direction with the exception of the central portion in the width direction overlapping the inner body 200.

As the intermediate portion resilient and elastic members 16, about 2 to 10 rubber threads with a thickness of about 155 to 1880 dtex, in particular about 470 to 1240 dtex (this is applied to a synthetic rubber, and in the case of a natural rubber, a cross-section area of 0.05 to 1.5 mm$^2$, in particular about 0.1 to 1.0 mm$^2$) are preferably fixed at an extension ratio of 150 to 300%, in particular 180 to 260%, and at intervals of 5 to 40 mm, in particular 5 to 20 mm.

When the lower waist portion resilient and elastic members 15 and the intermediate portion resilient and elastic members 16 are provided on the both sides of the central portion in the width direction with the exception of some or all of the portion overlapping the inner body 200 as illustrated in the drawings, the inner body 200 does not contract more than necessary in the width direction, does not become fluffy with deterioration in appearance, or does not decrease in absorbing performance. The foregoing mode includes the mode in which the resilient and elastic members reside only on the width-direction both sides, and the mode in which the resilient and elastic members reside crossing over the inner body 200 from one to the other sides in the width direction, but the resilient and elastic members are finely cut and exert no contraction force on some or all of the portion overlapping the inner body 200 (this substantially means that no resilient and elastic members are provided), and thus the contraction force of the resilient and elastic members acts only on the width-direction both sides. As a matter of course, the arrangement modes of the lower waist portion resilient and elastic members 15 and the intermediate portion resilient and elastic members 16 are not limited to the foregoing ones. Alternatively, some or all of the lower waist portion resilient and elastic members 15 and the intermediate portion resilient and elastic members 16 may be provided crossing over the inner body 200 from the one to the other sides in the width direction so that the contraction force entirely acts on the portions including the portion overlapping the inner body 200 in the width direction.

(Outer Body Separation Structure)

In the foregoing example, the integral outer body 12 covers continuously from the front panel F to the back panel B. Alternatively, the outer body 12 may be configured such that a ventral-side outer body and a dorsal-side outer body are discontinued and separated from each other at the crotch side (not illustrated). In that case, a crotch portion outer body may be stuck to the outer surface of the inner body to cover the portion exposed between the ventral-side outer body and the dorsal-side outer body. For the crotch portion outer body, the same material can be used as that for the foregoing outer body.

(About a Stretchable Structure)

Figure 1:
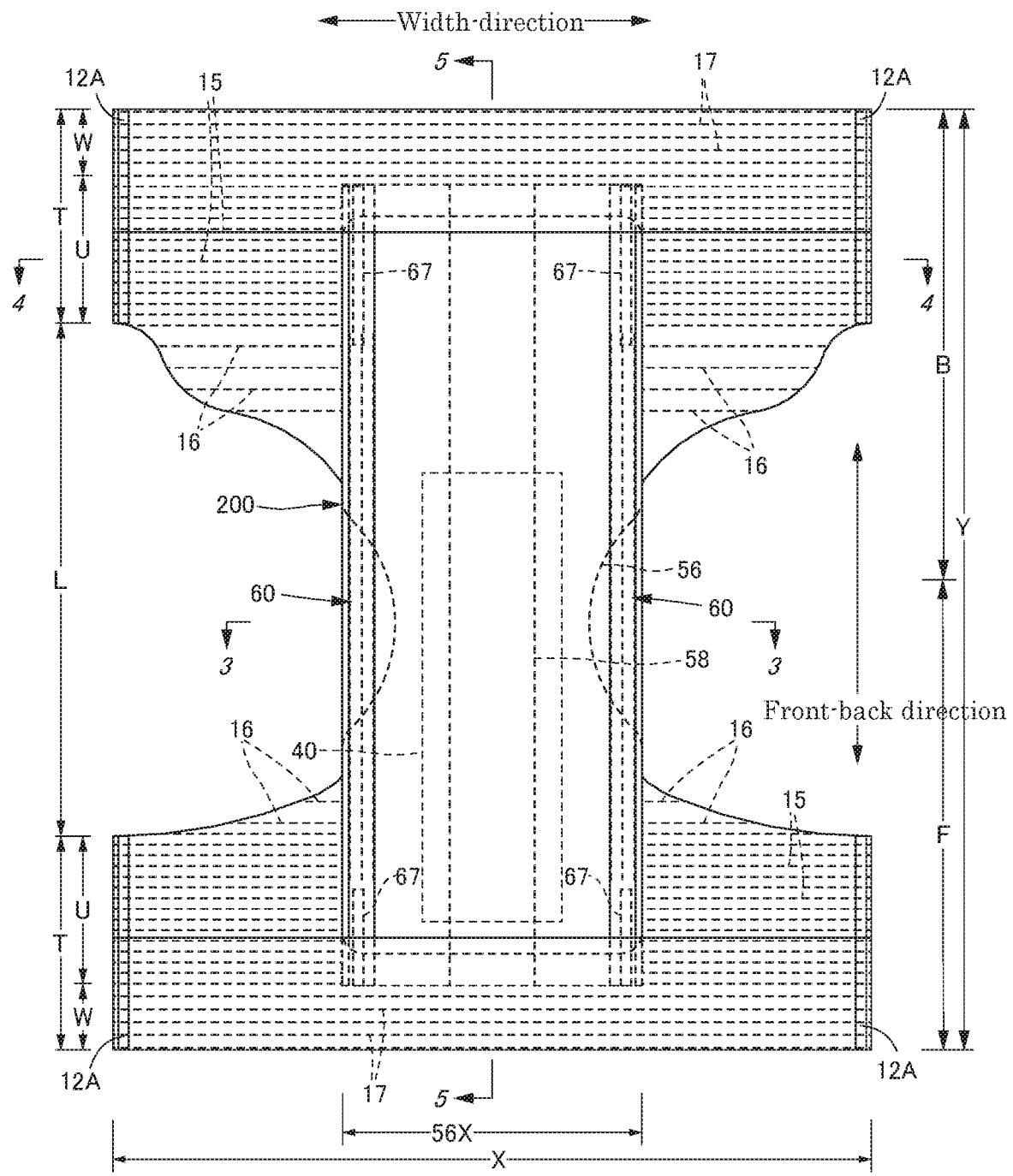
FIG. 1 is a plane view of an inner surface of a pants-type disposable diaper in an opened state.
Figure 2:
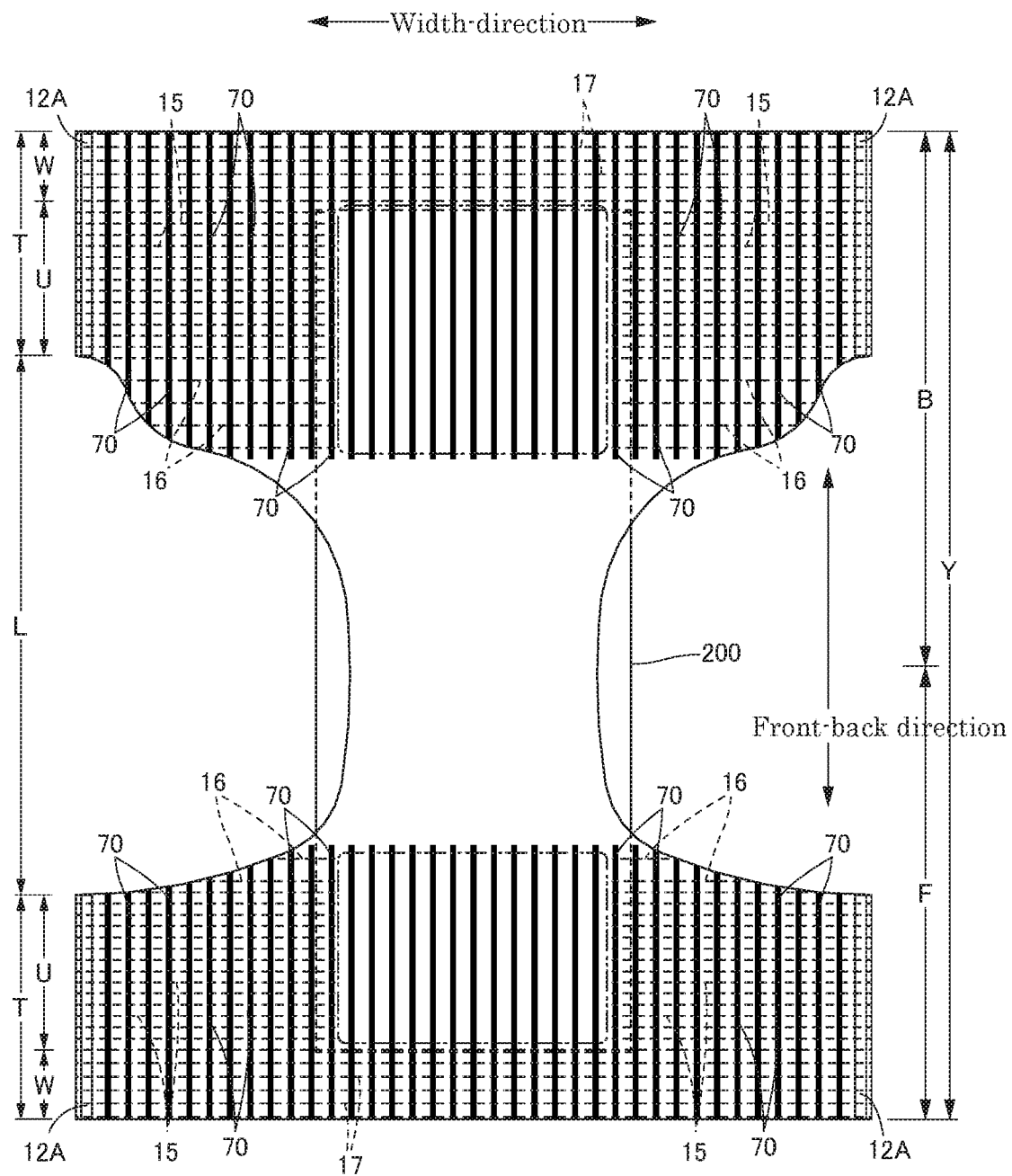
FIG. 2 is a plane view of an outer surface of the pants-type disposable diaper in the opened state.

In the pants-type disposable diaper illustrated in FIG. 2, a stretchable structure of the present invention is employed in the area ranging from the waist portion W to the intermediate portion L. Specifically, as illustrated in FIG. 6, the first sheet layer 21 and the second sheet layer 22 are joined together by a welding process that is intermittent in the extending direction and is continuous with a predetermined width in the direction crossing the extending direction (the direction orthogonal to the extending direction in the illustrated mode) to form sheet joined sections 70. Welded portions are shown with reference sign 75.

There is no limitation on the material for the first sheet layer 21 and the second sheet layer 22 as far as they are joined together by the welding process. In particular, nonwoven fabric with a thickness of 0.1 to 1 mm and a basis weight of 10 to 20 g/m$^2$ is desired. The first sheet layer 21 and the second sheet layer 22 may be formed by separate sheet materials 12S and 12H as the lower waist portion U and the intermediate portion L, or may be formed by folded parts of a single sheet material 12S as the waist portion W. In addition, the first sheet layer 21 and the second sheet layer 22 may be formed from single sheet materials, or either or both of them may be a laminated body of a plurality of sheet materials.

As the welding process, any of publicly known methods such as heat seal or ultrasound welding can be employed. In this case, the mode in which the welding process for forming the sheet joined sections 70 is continuous means the mode in which the first sheet layer 21 and the resilient and elastic members are welded, the second sheet layer 22 and the resilient and elastic members are welded, and thus the first sheet layer 21 and the second sheet layer 22 are welded indirectly to make the welding continuous as illustrated in FIG. 6(*d*).

The resilient and elastic members 19 are fixed to the first sheet layer 21 and the second sheet layer 22 by the welding process for forming the sheet joined sections 70 in positions crossing the sheet joined sections 70. That is, the first sheet layer 21 and the second sheet layer 22 are melted and welded to the resilient and elastic members 19 by the welding process, and as a result, the resilient and elastic members are fixed without melting.

Intervals 19*d* between the adjacent resilient and elastic members 19 can be decided as appropriate. However, when the intervals 19*d* exceed 10 mm, the thickness of the pleats 80 changes in the direction crossing the extending direction although not so much as in the vertical intermittent joined form, and the pleats 80 become fluffy. Accordingly, the intervals 19*d* between the adjacent resilient and elastic members 19 are preferably 10 mm or less, in particular 3 to 7 mm.

The thickness and extension ratio (in the state in which the stretchable structure is fully opened) of the resilient and elastic members 19 can be selected as appropriate according to the attachment positions of the resilient and elastic members 19. The preferred range is as described above. In general, the thickness of the resilient and elastic members 19 is desirably about 300 to 1000 dtex, and the extension ratio of the resilient and elastic members 19 is desirably about 200 to 350%.

In the stretchable structure described above, along with the contraction of the resilient and elastic members 19, the portions of the first sheet layer 21 and the second sheet layer 22 positioned between the sheet joined sections 70 contract and swell in the opposite directions to form the pleats 80 as illustrated in FIG. 6(*b*). Although FIG. 6(*b*) illustrates the natural length state, the resilient and elastic members 19 are extended to some extent when the diaper is worn, and the pleats 80 spread at the bottoms and height 80*h* of the pleats 80 becomes smaller as illustrated in FIG. 6(*c*). In addition, the stretchable structure is formed in the vertical continuous joined form, and the pleats 80 are extended linearly along the sheet joined sections 70. Accordingly, the stretchable structure is excellent in air permeability and appearance.

Characteristically, in the natural length state, an apparent thickness t1 of the sheet joined sections 70 of the second sheet layer 22 in positions overlapping the centers of the resilient and elastic members 19 is 80 to 100% of an apparent thickness t2 of the same in positions without the resilient and elastic members 19. This range is more preferably 95 to 100%. Accordingly, the second sheet layer 22 with the smaller thickness difference is thicker than the conventional one at the portions covering the resilient and elastic members 19. This provides a cushioning texture and makes the resilient and elastic members 19 softer. The same results can be obtained even when the sheet is stretched to some extent during use.

In the illustrated mode, the thickness difference in the second sheet layer 22 at the sheet joined sections 70 is made smaller. Instead of or in addition to this, the thickness difference in the first sheet layer 21 may be made smaller. In the case where the thickness difference in either the first sheet layer 21 or the second sheet layer 22 is to be made smaller, decreasing the thickness difference in the sheet layer on the skin side makes it possible to enhance the effect of improving the hand feeling for the wearer.

The structure with the smaller thickness difference can be formed by the method described later. The sheet layer in contact with the grooves enters into the grooves at the time of pressurization and heating, and the sheet layer of the portions having the resilient and elastic members 19 becomes longer in the direction crossing the resilient and elastic members 19, and the thickness difference in the sheet layer described above becomes small both in the natural length state and the worn state.

The shape of the sheet joined sections 70 can be decided as appropriate, but the sheet joined sections 70 are preferably continuous with a predetermined width in the direction crossing the extending direction (the direction orthogonal to the extending direction in the illustrated mode) as in the illustrated mode. A width 70*w* of the sheet joined sections 70 in the extending direction can be decided as appropriate, but is preferably about 1 to 4 mm (more preferably about 1 to 2 mm). Intervals 70*d* between the adjacent sheet joined sections 70 can be decided as appropriate, but is preferably about 4 to 8 mm (more preferably about 5 to 7 mm). The width 70*w* of the sheet joined sections 70 in the extending direction has influence on the intervals between the adjacent pleats 80. In the case where the pleats 80 are thin as in the vertical continuous joined form, when the width 70*w* exceeds 4 mm, the intervals between the adjacent pleats 80 become too wide, and the individual pleats 80 look independently. In addition, when the pleats 80 are deformed in such a manner as to be crushed and spread or fallen by the compression force in the thickness direction, the adjacent pleats 80 support each other more weakly. As a result, the pleats 80 become weaker in resistance to the deformation and restoration from the deformation, which provides insufficient fullness.

In addition, when the width 70*w* of the sheet joined sections 70 in the extending direction is set to 1 to 4 mm and the intervals 70*d* between the adjacent sheet joined sections 70 are set to be smaller than 4 mm or larger than 8 mm, the following situations will occur. That is, the intervals between the adjacent sheet joined sections 70 have influence on the height 80*h* and the width of the pleats 80: when the intervals are about 2 mm, the pleats 80 become less continuous in the vertical direction as if the pleats 80 are continuously fixed in the extending direction (it is meaningless to provide the sheet joined sections 70 intermittently in the extending direction), and when the interval is 3 mm, the pleats 80 extend linearly in the direction orthogonal to the extending direction but it cannot be expected that the adjacent pleats 80 support each other, and as a result, the fullness becomes insufficient. In addition, when the intervals between the sheet joined sections 70 exceed 8 mm, the pleats 80 get crushed irregularly by the compression during packaging, thereby deteriorating the appearance of the product. In contrast, only when the width 70*w* of the sheet joined sections 70 in the extending direction is set to 1 to 4 mm and the intervals 70*d* between the sheet joined sections 70 are set to 4 to 8 mm, it is possible to provide sufficient fullness and make the pleats 80 less prone to get crushed irregularly by the compression during packaging. In addition, when the sheet joined sections 70 are formed by welding in the vertical continuous joined form, the welded portions 75 become hard inevitably. However, the influence of the hardening is small when the dimensions of the sheet joined sections 70 fall within the foregoing ranges. Further, as a secondary effect, the welded portions 75 are higher in transparency to produce the outer appearance in which the glossy welded portions 75 form a striped pattern.

As another preferred shape of the sheet joined sections 70, the sheet joined sections 70 may have the shape of the welding process portions formed by various joint convex portions illustrated in FIG. 14 described later (that is, the same shape as that of the joint convex portions) to improve the stability of the manufacture by the method described later.

On the other hand, when the fixing force of the resilient and elastic members 19 is not sufficient, the resilient and elastic members 19 may come off. In particular, the width 70w of the sheet joined sections 70 in the extending direction is desirably small, but in this case, the portions where the resilient and elastic members 19 and the sheet joined sections 70 cross become smaller. Accordingly, it is necessary to fix the resilient and elastic members 19 in such small portions and it is important to provide the fixing force of the resilient and elastic members 19.

Figure 9:
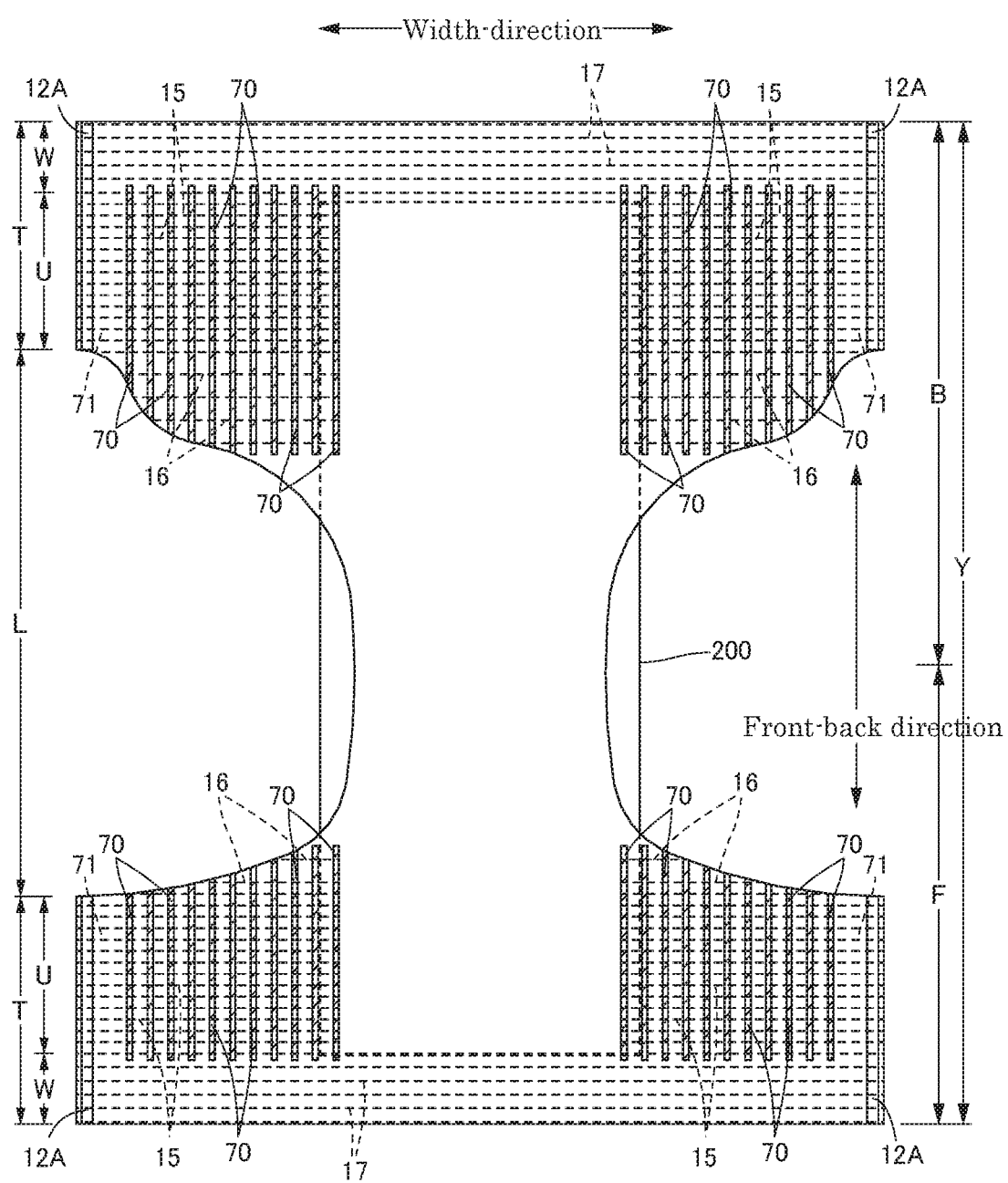
FIG. 9 is a plane view of an outer surface of a pants-type disposable diaper in the opened state.
Figure 10:
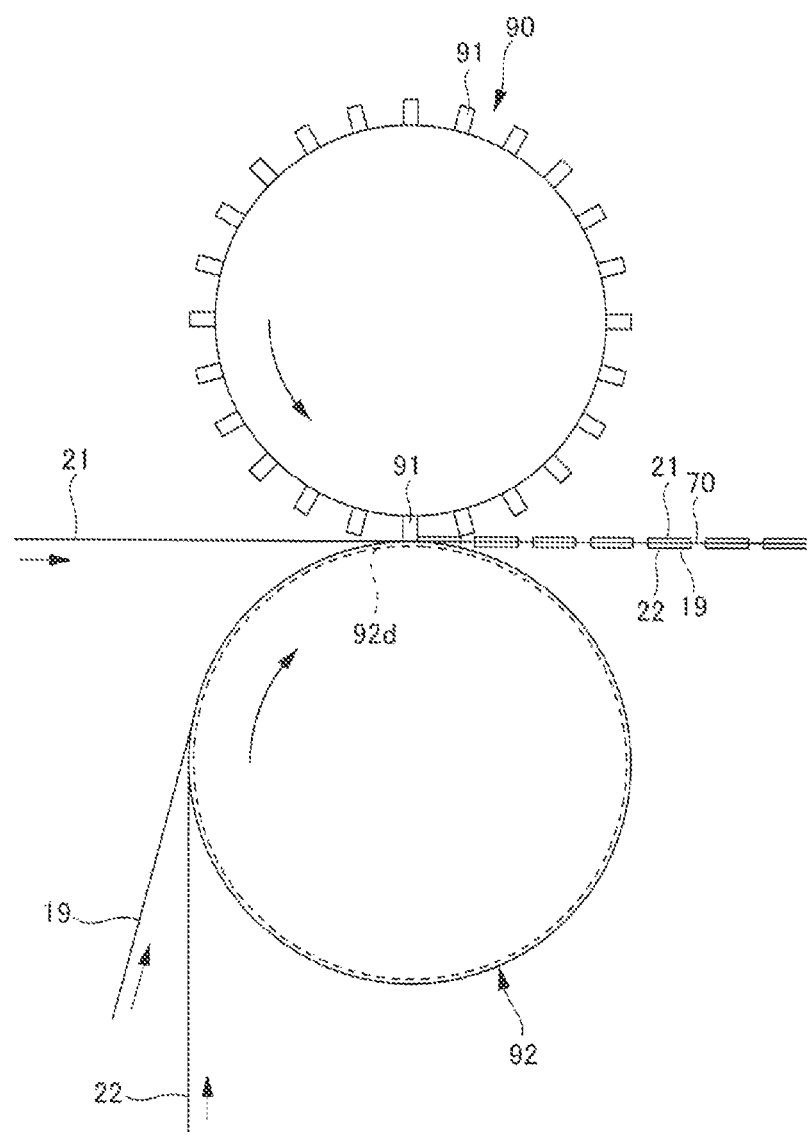
FIG. 10 is a schematic diagram illustrating a formation step of the stretchable structure.

Accordingly, in a preferred mode, the fixation of the resilient and elastic members 19 to the first sheet layer 21 and the second sheet layer 22 is reinforced in the positions crossing the sheet joined sections 70 or other positions. For example, as illustrated in FIG. 9, a reinforcement adhesive 71 such as a hot-melt adhesive 71 is applied to at least one of the first sheet layer 21 and the second sheet layer 22 in regions where the both ends of the resilient and elastic members 19 are positioned to reinforce the fixation of the resilient and elastic members 19 to the first sheet layer 21 and the second sheet layer 22 by the adhesive 71 as illustrated in FIG. 9.

The width-direction outer ends of the resilient and elastic members 19 of the outer body 12 in the pants-type disposable diaper are firmly fixed by the side seal portions 12A. Accordingly, in a preferred mode, the foregoing fixation reinforcement means may be omitted in the end regions on the side seal portion 12A sides.

(Others)

In the example illustrated in FIG. 2, the stretchable structure of the present invention is applied to the entire stretchable region of the outer body of the pants-type disposable diaper. The stretchable structure of the present invention is also applied to only the region from the lower waist portion U to the intermediate portion L of the pants-type disposable diaper or only the lower waist portion or the intermediate portion. In addition, the resilient and elastic members 16 in the intermediate portion L may be omitted. Further, the foregoing stretchable structure is also applied to other stretchable portions such as the waist portion on the back side of the tape-type disposable diaper described above in relation to the conventional technique, and the three-dimensional gathers.

<About the Method for Forming the Stretchable Structure>

Next, the method for forming the stretchable structure for the absorbent article illustrated in FIGS. 10 to 13 will be described. According to the method for forming the stretchable structure for the absorbent article, basically, while the first roll 90 with joint convex parts 91 provided at circumferential intervals on the outer peripheral surface and the second roll 92 opposed to the first roll 90 and having a circular outer peripheral surface are rotated in opposite directions around axis centers thereof, the first sheet layer 21, the second sheet layer 22, and the elongated resilient and elastic members 19 continuously disposed in the MD direction (sheet transfer direction) between the two sheet layers are passed between the first roll 90 and the second roll 92, and the first sheet layer 21 and the second sheet layer 22 sandwiched between the joint convex parts 91 of the first roll 90 and the second roll 92 are pressurized and heated to form the sheet joined sections 70 by welding the first sheet layer 21 and the second sheet layer 22 in such a manner as to cross the resilient and elastic members 19 and have MD-direction intervals therebetween. The heating means may be frictional heating (ultrasound seal) by ultrasound vibrations of the first roll 90 or heat transfer (heat seal) via the first roll 90 and the second roll 92.

Figure 11:
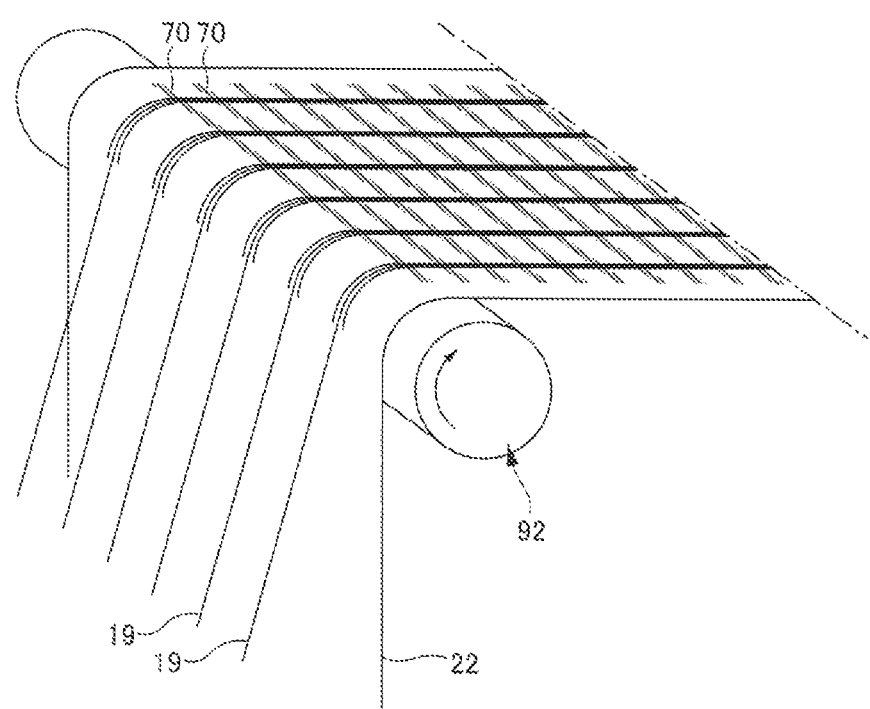
FIG. 11 is a schematic perspective diagram illustrating a pressurization and heating step in which a first roll and a first sheet are not shown.
Figure 12:
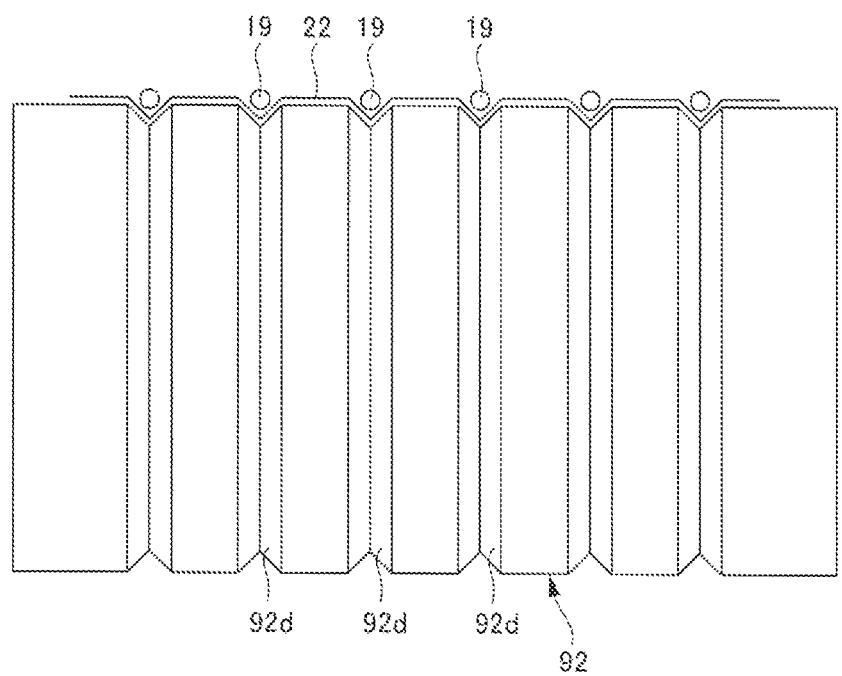
FIG. 12 is a front view of main components before pressurization and heating.
Figure 13:
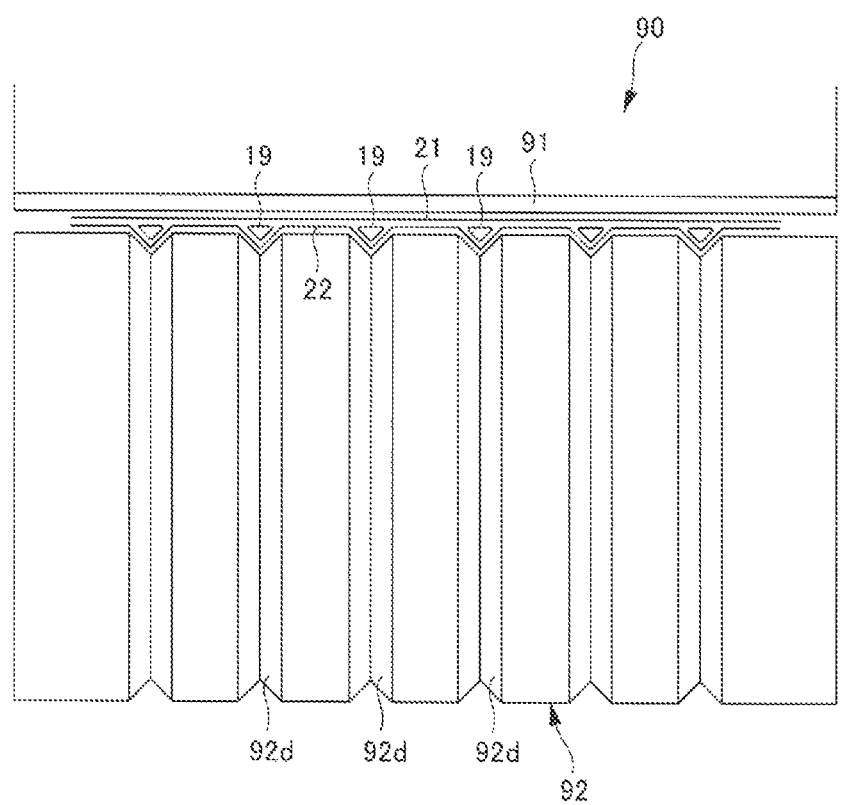
FIG. 13 is a front view of the main components during pressurization and heating.

Characteristically, the circumferentially continuous grooves 92d are formed circumferentially on the entire outer peripheral surface as the pressurization surface of the second roll 92, and at the time of pressurization and heating, the passage sections of the resilient and elastic members 19 are pressurized and heated in the positions including the grooves 92d and the non-passage sections of the resilient and elastic members 19 are pressurized and heated in the positions not including the grooves 92d, as illustrated in FIG. 13. Accordingly, the difference between the pressure applied to the first sheet layer 21 and the second sheet layer 22 in the non-passage sections of the resilient and elastic members 19 and the pressure applied to the first sheet layer 21, the resilient and elastic members 19, and the second sheet layer 22 in the passage sections of the resilient and elastic members 19 becomes smaller, and thus the variation in welding quality is decreased. However, the pressure applied to the resilient and elastic members 19 becomes lower, thereby making the cutting of the resilient and elastic members less to occur. At that time, as illustrated in FIGS. 11 to 13, the second sheet layer 22 in contact with the grooves 92d enters into the grooves 92d, the second sheet layer 22 with the resilient and elastic members 19 becomes longer in the direction crossing the resilient and elastic members 19, and the thickness difference in the second sheet layer 22 becomes small both in the natural length state and the worn state as described above.

In the illustrated mode, the grooves 92d are formed only on the pressurization surface of the second roll 92. Instead of or in addition to this, the circumferentially continuous grooves 92d may be formed on the pressurization surface of the first roll 90 (that is, the tip surfaces of the joint convex parts 91). In this case, the first sheet layer 21 enters into the grooves 92 on the first roll 90, the first sheet layer 21 with the resilient and elastic members 19 becomes longer in the direction crossing the resilient and elastic members 19, and the thickness difference in the first sheet layer 21 becomes small both in the natural length state and the worn state as described above. In addition, in the illustrated mode, there are no convex and concave portions on the outer peripheral surface of the second roll 92. Alternatively, the joint convex parts 91 may also be provided on the outer peripheral surface of the second roll 92 in positions corresponding to the joint convex parts 91 on the first roll 90.

As in the illustrated mode, the resilient and elastic members 19 are preferably guided to wrap around the roll having the grooves 92d (the second roll 92 in the illustrated mode) as illustrated in FIG. 12 at a stage before the pressurization and heating because the sheet layer in contact with the resilient and elastic members 19 and the grooves 92d (the second sheet layer 22 in the illustrated mode) is brought into the pressurization and heating process in the state in which the sheet layer is pressed into the grooves 92d by line tension. In addition, the sheet layer not in contact with the grooves 92d (the first sheet layer 21 in the illustrated mode) is preferably guided to wrap around the roll without the grooves 92d from the direction of the tangent to the heating and pressurization position so as not to wrap around the roll with the grooves 92d.

Figure 14A:
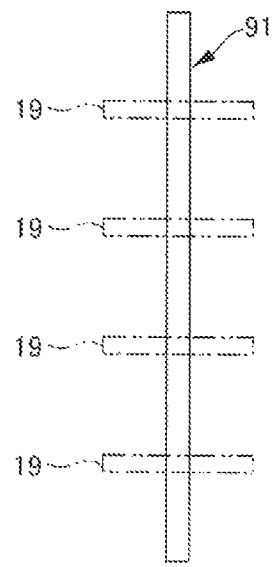
FIGS. 14(a) to 14(e) are plane views of shape examples of joint convex parts.
Figure 14B:
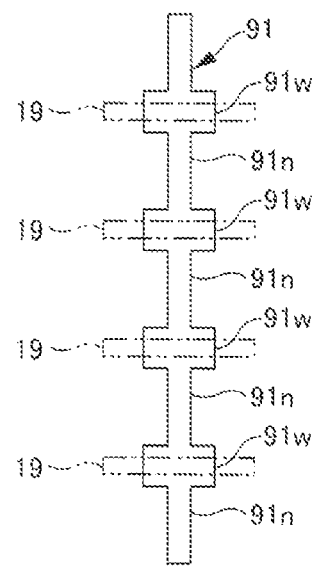

The joint convex parts 91 may be elongated and extended with a specific width in the direction crossing the resilient and elastic members 19 as illustrated in FIG. 14(a) or may be formed in the modes illustrated in FIGS. 14(b) to 14(e). Specifically, the joint convex parts 91 illustrated in FIG. 14(b) are elongated and extended in the direction crossing the resilient and elastic members 19 and have first portions 91w relatively long in the circumferential direction and second portions 91n relatively short in the circumferential direction, and the first portions 91w are positioned in sections including the passage sections of the resilient and elastic members 19, and the second portions 91n are positioned in sections not including the passage sections of the resilient and elastic members 19. By forming the joint convex parts 91 in such a shape as described above, it is possible to further decrease the pressure applied to the passage sections of the resilient and elastic members 19, thereby further enhancing the effect of cutting prevention. The same effect could be produced by making the grooves 92d deeper, but in this case, the pressurization and heating of the passage sections of the resilient and elastic members 19 would be likely to be insufficient. Accordingly, the shape of the joint convex parts 91 is changed in a preferred mode. In the illustrated mode, the first portions 91w protrude to the both sides of the rotational direction relative to the second portions 91n, but the first portions 91w protrude only to one of the sides.

Figure 14C:
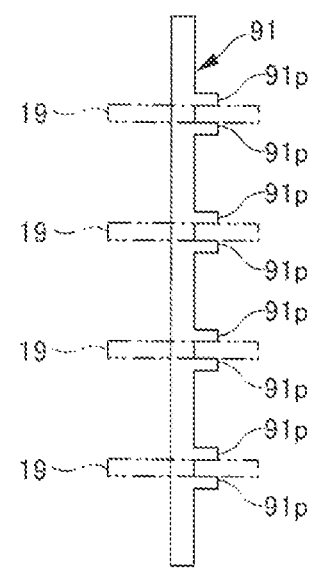
Figure 14D:
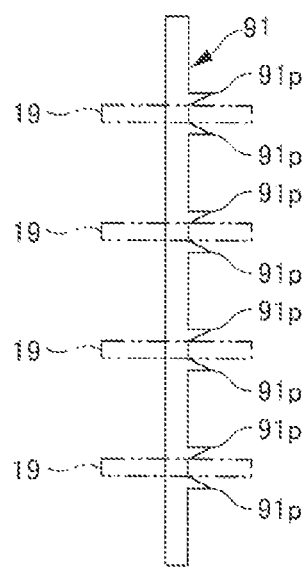
Figure 14E:
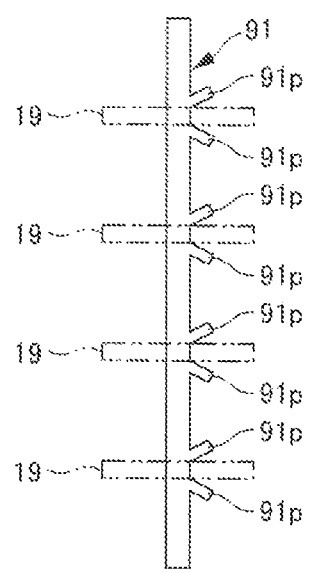

As illustrated in FIGS. 14(c) to 14(e), in a preferred mode, the joint convex parts 91 are elongated and extended in the direction crossing the resilient and elastic members 19 and have protrusion parts 91p protruding from CD-direction (orthogonal to the MD direction) both sides of sections crossing the resilient and elastic members 19 in the rotational direction. By forming the joint convex parts 91 in such a shape as described above, the resilient and elastic members 19 are guided to a space between the protrusion parts 91p, thereby preferably allowing the passage sections of the resilient and elastic members 19 to be reliably located in the positions including the grooves 92d. In particular, the intervals between the protrusion parts 91p preferably increase continuously (or intermittently) with increasing proximity to the rotational direction side as illustrated in FIG. 14(d). The intervals between the protrusion parts 91p may be larger than the thickness of the resilient and elastic members 19 as in the illustrated mode or may be smaller than the thickness of the resilient and elastic members 19 to obtain the same advantage.

Figure 15:
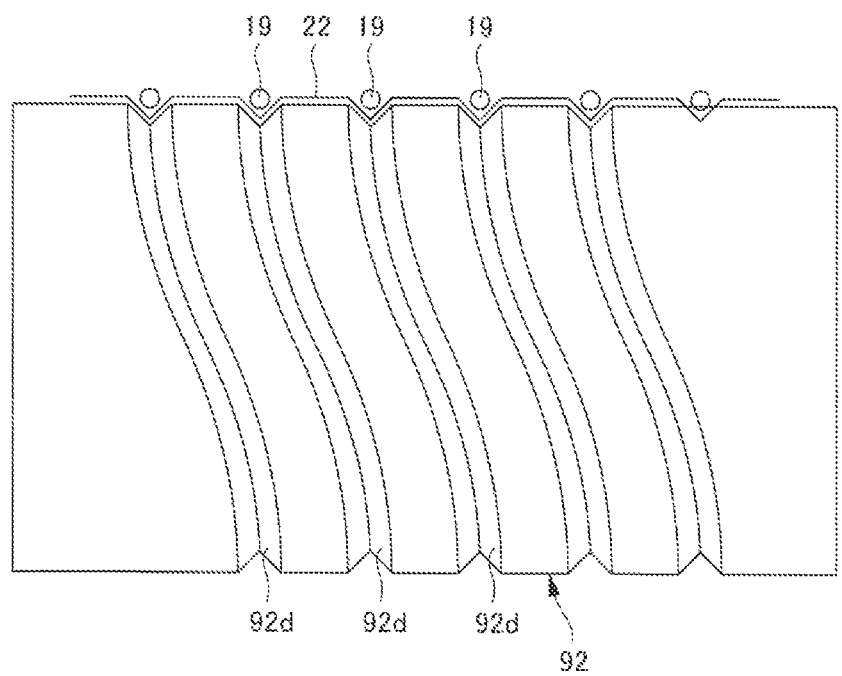
FIG. 15 is a front view of a second roll.

The CD-direction (orthogonal to the MD direction) positions of the grooves 92d may be constantly linear in the circumferential direction as illustrated in FIG. 12 or may be curved as illustrated in FIG. 15 depending on the arrangement shape of the resilient and elastic members 19 (whether linear in the MD direction or curved). There is no limitation on the cross-section shape of the grooves 92d, and the cross-section shape of the grooves 92d may be an inverted triangle as in the illustrated mode, or may be a rectangle, a semicircle, or a U shape.

The grooves 92d may be provided in the entire rotation periods (that is, the entire peripheries) of the first roll 90 and the second roll 92 as in the illustrated mode or may be provided only in partial ranges of the rotation periods. For example, in the pants-type disposable diaper described above, the resilient and elastic members 19 need to be passed through some regions of the outer body 12 such as a region overlapping the absorber 56 due to a manufactural reason, but the elasticity of the resilient and elastic members 19 is unnecessary in these regions and the resilient and elastic members 19 are finely cut in the regions to make their elasticity disable. Accordingly, in the region to be provided with elasticity, the cutting of the resilient and elastic members 19 by the welding process of the first sheet layer 21 and the second sheet layer 22 is prevented by the use of the grooves 92d on the pressurization surface, and in the region not in need of the elasticity, the resilient and elastic members 19 are cut by the welding process without the grooves 92d on the pressurization surface. This allows the formation of the sheet joined sections 70 and the cutting of the resilient and elastic members 19 at the same time, thereby simplifying the manufacturing process. That is, the grooves 92d are formed in partial ranges of the rotation periods of the first roll 90 and the second roll 92, and the grooves 92d are not formed in the other ranges of the rotation periods of the first roll 90 and the second roll 92 so that the resilient and elastic members 19 can be cut by the pressurization and heating in the range with the grooves 92d and the resilient and elastic members 19 are not cut at the time of the pressurization and heating in the range without the grooves 92d.

<Descriptions of the Terms Used Herein>

Unless otherwise specified herein, the terms used herein have the meanings described below.

The "front-back (vertical) direction" refers to the direction linking the ventral side (front side) and the dorsal side (rear side), and the "width direction" refers to the direction (right-left direction) orthogonal to the front-back direction.

The "extension ratio" refers to a value with respect to 100% representing the natural length.

The "basis weight" is measured in such a manner as described below. That is, a sample or a test piece is preliminarily dried and left stand in a test room or a test device in a standard state (at a temperature of 20±5° C. and a relative humidity of 65% or less) until reaching a constant weight. The preliminary drying refers to turning the sample or the test piece to a constant weight in an environment at a relative humidity of 10 to 25% and a temperature not exceeding 50° C. The preliminary drying is not necessary for fibers with an official moisture regain of 0.0%. The test piece of the constant weight is cut into a 200 mm×250 mm (±2 mm) sample by the use of a basis weight plate (200 mm×250 mm±2 mm). The weight of the sample is measured and the measured value is multiplied by 20 to determine the weight per square meter as a basis weight.

The "thickness" is automatically measured by an automated thickness gauge (KES-G5 handy compression measurement program) on the conditions that the load is 10 gf/cm$^2$ and the pressure area is 2 cm$^2$).

The water absorption capacity is measured by carrying out JIS K7223-1996 "Testing method for water absorption capacity of super absorbent polymers."

The water absorption rate is determined as "time that elapses before the end point" by carrying out JIS K7224-1996 "Testing method for water absorption rate of super absorbent polymers" using 2 g of high absorbent polymer and 50 g of saline.

When there are no descriptions of environmental conditions for tests and measurements, the tests and measurements are performed in a test room or a test device in a standard state (at a temperature of 20±5° C. and a relative humidity of 65% or less).

INDUSTRIAL APPLICABILITY

The present invention is suited to pants-type disposable diapers in the foregoing examples but is also applicable to stretchable structures in tape-type or pad-type disposable diapers and other general absorbent articles such as sanitary napkins, and their manufacture.

REFERENCE SIGNS LIST

11 Liquid impervious sheet
12 Outer body
12A Side seal portion
12H Second sheet material
12S First sheet material
12r Folded part
200 Inner body
30 Top sheet
40 Interlayer sheet
50 Absorbent element
56 Absorber
58 Wrapping sheet
60 Three-dimensional gather
62 Gather sheet
70 Sheet joined sections
71 Adhesive
75 Welded portion
80 Pleat
21 First sheet layer
22 Second sheet layer
15 Lower waist portion resilient and elastic member
16 Intermediate portion resilient and elastic member
17 Waist edge portion resilient and elastic member
19 Resilient and elastic member
90 First roll
91 Joint convex part
92 Second roll
92d Groove

The invention claimed is:

1. A method for forming a stretchable structure for an absorbent article, comprising:
    while rotating a first roll with joint convex parts provided at circumferential intervals on an outer peripheral surface and a second roll opposed to the first roll, in opposite directions around axis centers thereof, passing a first sheet layer, a second sheet layer, and elongated resilient and elastic members continuously disposed in an MD direction between these sheet layers, between the first roll and the second roll; and
    pressurizing and heating by sandwiched between the joint convex parts of the first roll and the second roll to form sheet joined sections welding the first sheet layer and the second sheet layer in such a manner as to cross the resilient and elastic members and have MD-direction intervals therebetween,
    wherein the joint convex parts extend continuously in a direction crossing the resilient and elastic members and perpendicular to the MD direction,
    wherein circumferentially continuous grooves are formed on a pressurization surface of only the second roll in a partial range of a rotation period of the second roll,
    one of the first sheet layer and the second sheet layer is in contact with the second roll having the grooves and the resilient and elastic members are guided to wrap around the second roll having the grooves, the resilient and elastic members and the one of the first sheet layer and the second sheet layer in contact with the grooves are pressed into the grooves by line tension before the first sheet layer and the second sheet layer are pressurized and heated, and
    under the pressurization and heating, passage sections of the resilient and elastic members are pressurized and heated in positions including the grooves and non-passage sections of the resilient and elastic members are pressurized and heated in positions not including the grooves.

2. A method for forming a stretchable structure for an absorbent article, comprising:
    while rotating a first roll with joint convex parts provided at circumferential intervals on an outer peripheral surface and a second roll opposed to the first roll, in opposite directions around axis centers thereof, passing a first sheet layer, a second sheet layer, and elongated resilient and elastic members continuously disposed in an MD direction between these sheet layers, between the first roll and the second roll; and
    pressurizing and heating by sandwiched between the joint convex parts of the first roll and the second roll to form sheet joined sections welding the first sheet layer and the second sheet layer in such a manner as to cross the resilient and elastic members and have MD-direction intervals therebetween, wherein
    the joint convex parts are elongated and extended in a direction crossing the resilient and elastic members and have first portions relatively long in a circumferential direction and second portions relatively short in the circumferential direction,
    the first portions are positioned in sections including passage sections of the resilient and elastic members, and
    the second portions are positioned in sections not including the passage sections of the resilient and elastic members,
    circumferentially continuous grooves are formed on a pressurization surface of at least one of the first roll and the second roll in a partial range of a rotation period of the first roll and the second roll,
    under the pressurization and heating, the passage sections of the resilient and elastic members are pressurized and heated in positions including the grooves and non-passage sections of the resilient and elastic members are pressurized and heated in positions not including the grooves.

3. The method for forming a stretchable structure for an absorbent article according to claim 1, wherein the joint convex parts have protrusion parts protruding in a rotational direction crossing the resilient and elastic members.

4. The method for forming a stretchable structure for an absorbent article according to claim 1, wherein
    the grooves are formed in a partial range of a rotation period of the second roll but no groove is formed in other ranges, and
    the resilient and elastic members are cut by the pressurization and heating in the other ranges without the grooves and the resilient and elastic members are not cut in the range with the grooves at the time of the pressurization and heating.

* * * * *